US010870834B2

(12) United States Patent
Dekel et al.

(10) Patent No.: US 10,870,834 B2
(45) Date of Patent: Dec. 22, 2020

(54) ISOLATED POPULATIONS OF ADULT RENAL CELLS AND METHODS OF ISOLATING AND USING SAME

(71) Applicants: TEL HASHOMER MEDICAL RESEARCH INFRASTRUCTURE AND SERVICES LTD., Ramat-Gan (IL); RAMOT AT TEL-AVIV UNIVERSITY LTD., Tel-Aviv (IL)

(72) Inventors: Benjamin Dekel, Tel Aviv (IL); Orit Harari-Steinberg, Raanana (IL); Ella Buzhor, Rishon Lezion (IL)

(73) Assignees: TEL HASHOMER MEDICAL RESEARCH INFRASTRUCTURE AND SERVICES LTD., Ramat Gan (IL); RAMOT AT TEL-AVIV UNIVERSITY LTD., Tel Aviv (IL)

(*) Notice: Subject to any disclaimer, the term of this patent is extended or adjusted under 35 U.S.C. 154(b) by 44 days.

(21) Appl. No.: 16/045,784

(22) Filed: Jul. 26, 2018

(65) Prior Publication Data
US 2018/0346882 A1 Dec. 6, 2018

Related U.S. Application Data

(62) Division of application No. 13/697,531, filed as application No. PCT/IL2011/000376 on May 12, 2011, now abandoned.

(60) Provisional application No. 61/457,613, filed on May 2, 2011, provisional application No. 61/334,206, filed on May 13, 2010.

(51) Int. Cl.
*C12N 5/071* (2010.01)

(52) U.S. Cl.
CPC ........ *C12N 5/0686* (2013.01); *C12N 2500/90* (2013.01); *C12N 2501/11* (2013.01); *C12N 2501/115* (2013.01); *C12N 2501/33* (2013.01); *C12N 2501/392* (2013.01); *C12N 2533/40* (2013.01)

(58) Field of Classification Search
CPC .............. C12N 5/0686; C12N 2500/90; C12N 2501/11; C12N 2501/115; C12N 2501/33; C12N 2501/392; C12N 2533/40
See application file for complete search history.

(56) References Cited

U.S. PATENT DOCUMENTS

| | | |
|---|---|---|
| 2002/0102241 A1 | 8/2002 | Arnaout et al. |
| 2002/0119596 A1 | 8/2002 | Clarke et al. |
| 2004/0014209 A1 | 1/2004 | Lassar et al. |
| 2005/0026023 A1 | 2/2005 | Hirai et al. |
| 2007/0031966 A1 | 2/2007 | Dressler et al. |
| 2007/0065942 A1 | 3/2007 | Wandinger-Ness et al. |
| 2010/0097794 A1 | 4/2010 | Teng et al. |
| 2011/0311494 A1 | 12/2011 | Benjamin et al. |
| 2011/0311495 A1 | 12/2011 | Dekel |
| 2014/0011280 A1 | 1/2014 | Dekel et al. |
| 2015/0139963 A1 | 5/2015 | Dekel et al. |
| 2018/0042965 A1 | 2/2018 | Dekel et al. |

OTHER PUBLICATIONS

Histology Study Guide: Kidney and Urinary Tract. downloaded from www.siumed.edu/~dking2/crr/rnguide.htm. p. 1-14. (Year: 2019).*
Bussolati et al. Therapeutic use of human renal progenitor cells for kidney regeneration. Nat. Rev. Nephrol. 11, 695-706 (Year: 2015).*
Marcheque et al. Concise Reviews: Stem Cells and Kidney Regeneration: An Update. Stem Cells Translational Medicine 2019;8:82-92 (Year: 2019).*
Hipp et al. "Sources of Stem cells for Regenerative Medicine". Stem Cell Reviews, XP002583273, 4(1):3-11, Apr. 2008. p. 7-8.
Hjelle et al. Drug Metabolism in Isolated Proximal Tubule Cells: Aledhyde Dehydrogenase. Journal of Pharmacology and Experimental Therapeutics, XP009139110, 224(3): 699-706, Mar. 1, 1983.
Hunagfu et al. "Induction of Pluripotent Stem Cells by Defined Factors is Greatly Improved by Small-Molecule Compounds". Nature Biotechnology, XP002502536, 26(7): 795-797, Jul. 1, 2008. p. 795-796.
Imai et al. "Inhibiton of Histone Deacetylase Activates Side Population Cells in Kidney and Partially Reverses Chronic Renal Injury", Stem Cells, XP002583269, 25(10): 2469-2475, 2007. p. 2469, 2473.
Jones et al. "Genomics of Renal Cell Cancer: The Biology Behind and Therapy Ahead". Clinical Cancer Research, 13(2 Suppl.): 685s-692s, Jan. 15, 2007.
Kim et al. "Improvement of Kidney Failure With Fetal Kidney Precursor Cell Transplantation". Transplantation, 83: 1249-1258, 2007.
Kim et al. "Kidney Tissue Reconstruction by Fetal Kidney Cell Transplantation: Effect of Gestation Stage of Fetal Kidney Cells". Stem Cells, 25:1392-1401, 2007.
Kobayashi et al. "Six2 Defines and Regulates a Multipotent Self-Renewing Nephron Progenitor Population Throughout Mammalian Kidney Development". Cell Stem Cell, 3: 169-181, 2008.
Kreidberg et al. "WT-1 is Required for Early Kidney Development". Cell, 74: 679=791, 1993.
Kretzler et al. "Integrin-Linked Kinase as a Candidate Downstream Effector in Proteinuria". The FASEB Journal, 15(10): 1843-1845, Aug. 2001.
Markovie-Lipkovski et al. "Neural Cell Adhesion Molecule Expression on Renal Interstitial Cells". Nephrology Dialysis Transplantation, XP002581531, 22:(6): 1558-1566, Jun. 2007. p. 1558, 1562-1565.
Metsuyanim et al. "Accumalation of Malignant Renal Stem Cells is Associated with Epigenetic Changes in Normal Renal Progenitor Genes". Stem Cells, 26: 1806-1817, 2008.
Metsuyanim et al. "Expression of Stem Cell Markers in the Human Fetal Kidney". PloS ONE, XP002581532, 4(8): e6709-1-e6709-15, Aug. 2009.

(Continued)

*Primary Examiner* — Taeyoon Kim
(74) *Attorney, Agent, or Firm* — JMB Davis Ben-David

(57) ABSTRACT

A method of generating a nephrospheroid is disclosed. The method comprises culturing human adult kidney cells in a culture medium under non-adherent conditions. Uses thereof and other renal cell populations are also disclosed.

12 Claims, 28 Drawing Sheets
(21 of 28 Drawing Sheet(s) Filed in Color)

(56) References Cited

OTHER PUBLICATIONS

Milutinovic et al. "Valproate Induces Widespread Epigenetic Reprogramming Which Involves Demethylation of Specific Genes". Carcinogenesis, 28(3): 650-571, 2007.
Miyamoto et al. "Cell-Free Extracts from Mammalian Oocytes Partially Induce Nuclear Reprogramming in Somatic Cells". Biology of Reproduction, XP002583272, 80(5):935-943, May 1, 2009. p. 936, 939.
Nishinakamura et al. "Kidney Development Conserved Over Species: Essential Roles of Sall1". Seminars in Cell Development and Biology, 14:241-247, 2003. Abstract.
Osafune et al. "Identification of Multipotent Progenitors in the Embryonic Mouse Kidney by a Novel Colony-Forming Assay". Development, XP002581530, 133(1):151-161, Jan. 2006. p. 153, Fig-1.
Rivera et al. "Wilms Tumor: Connecting Tumorigenesis and Organ Development in the Kidney". Nature Reviews: Cancer, 5: 699-712, 2005.
Rosenberg et al. "Stem Cells and the Kidney: Where Do We Go From Here?". Journal of the American Society of Nephrology, XP002581964, 18(12): 2018-3020, Dec. 2007. p. 3019.
Schmelzer et al. "The Phenotypes of Pluripotent Human Hepatic Progenitors". Stem Cells, XP002581966, 24(8): 1852-1858, Aug. 2006.
Schmidt-Ott et al. "WNT/Beta Catenin Signaling in Nephronic Progenitors and Their Epithelial Progeny". Kidney International, XP002602079, 74(8): 1004-1008, Oct. 2008.
Self et al. "Six2 is Required for Suppression of Nephrogenesis and Progenitor Renewal in the Developing Kidney". The EMBO Journal, 25: 5214-5228, 2006.
Senanayake et al. "The Pluripotent Renal Stem Cell Regulator Six2 is Activated in Renal Neoplasms and Influences Cellular Proliferation and Migration". Human Pathology, 44: 336-345, 2013.
Trzpis et al. "Epithelial Cell Adhesion Molecule. More Than a Carcinoma Marker and Adhesion Molecule". The American Journal of Pathology, XP002581967, 171(2): 386-396, Aug. 2007. p. 388-389, Table 2.
Trzpis et al. "Expression of EpCAM is Up-Regulated During Regeneration of Renal Epithelia". Journal of Pathology, XP002581968, 216(2): 201-208, Oct. 2008.
Weissmann et al. "Translating Stem and Progenitor Cell Biology to the Clinic: Barriers and Opportunities". Science, 287(5457): 1442-1446, Feb. 25, 2000.
Yoshikawa et al. "Inhibition of Histone Deacetylase Activity Suppresses Epithelial-to-Mesenchymal Transition Induced by TGF-[Beta]1 in Human Renal Epithelial Cells". Journal of the American Society of Nephrology, XP002583270, 18(1): 58-65. Jan. 2007. p. 58.
Zhong et al. "Spheres Derived from the Human SK-RC-42 Renal Cell Carcinoma Cell Line are Enriched in Cancer Stem Cells". Cancer Ilets, XP027451196, 299(2): 150-160, Dec. 28, 2010.
Pode-Shakked et al. 2009 Cover Page. downloaded from http://onlinelibrary.wiley.com/doi/10.1111/i.1582-4924.2008.00607.x/full. p. 1.
Eccles et al., Comparative in Situ Hybridization Analysis of PAX2, PAX8, and WT1 Gene Transcription in Human Fetal Kidney and Wilms' Tumours, American Journal of Pathology, vol. 146, No. 1, Jan. 1995.
Garvin et al., The In Vitro Growth, Heterotransplantation, and Immunohistochemical characterization of the Blasternal Component of Wilms' Tumour, American Journal of Pathology, vol. 129, No. 2, Nov. 1987.
Communication Pursuant to Article 94(3) EPC dated Jan. 22, 2014 From the European Patent Office Re. Application No. 11728406.7.
International Preliminary Report on Patentability dated Nov. 22, 2012 From the International Bureau of WIPO Rep. Application No. PCT/IL2011/000376.

International Search Report and the Written Opinion dated Sep. 26, 2011 From the International Search Authority Re. Application No. PCT/IL2011/000376.
Bussolati et al. "Isolation of Renal Progenitor Cells From Adult Human Kidney". American Journal of Pathology, XP002454238, 166(2): 545-555, Feb. 1, 2005.
Buzhor et al. "Kidney Spheroids Recapitulate Tubular Organoids Leading to Enhanced Tubulogenic Potency of Human Kidney-Derived Cells". Tissue Engineering Part A., XP55006582, 17(17-18): 2305-2319, Sep. 1, 2011.
Liu et al. "Suspended Aggregates as an Immobilization Mode for High-Density Perfusion Culture of HEK 293 Cells in a Stirred Tank Bioreactor". Applied Microbiology and Biotechnology, XP019441688, 72(6): 1144-1151, Mar. 28, 2006, p. 1147, Table 1.
Lusis et al. "Isolation of Clonogenic, Long-Term Self Renewing Embryonic Renal Stem Cells". Stem Cell Research XP027106369, 5(1): 23-29, Mar. 27, 2010. p. 27.
Maeshima et al. "Adult Kidney Tubular Cell Population Showing Phenotypic Plasticity, Tubulogenic Capacity, and Integration Capability into Developing Kidney". Journal of the American Society of Nephrology, XP002471868, 17(1): 188-198, Jan. 1, 2006.
Pode-Shakked et al. "Development Tumourigenesis: NCAM as a Putative Marker for the Malignant Renal Stem/Progenitor Cell Population". Journal of Cellular and Molecular Medicine, XP002581529, 13(8B): 1792-1808, Aug. 1, 2009. p. 1795, r-h Col., Fig.1.
Communication Pursuant to Article 94(3) EPC dated Nov. 29, 2016 From the European Patent Office Re. Application No. 11728406.7. (4 Pages).
Communication Pursuant to Article 94(3) EPC dated Oct. 24, 2016 From the European Patent Office Re. Application 10710685.8.
Official Action dated Oct. 26, 2016 From the US Patent and Trademark Office Re. U.S. Appl. No. 14/027,256.
Office Action dated Jun. 28, 2016 From the Israel Patent Office Re. Application No. 214837 and Its Translation Into English.
Communication Pursuant to Article 94(3) EPC dated Mar. 14, 2016 From European Patent Office Re. Application No. 11728406.7.
Official Action dated Feb. 2, 2016 From the US Patent and Trademark Office Re. U.S. Appl. No. 14/027,256.
Official Action dated Oct. 7, 2015 From the US Patent and Trademark Office Re. U.S. Appl. No. 14/027,256.
Hueber et al. "Pax2 Inactivation Enhances Cisplatin-Induced Apoptosis in Renal Carcinoma Cells", Kidney International, 69; 1139-1145, Published Online Feb. 15, 2006.
Nakagawa et al. "Generation of Induced Pluripotent Stem Cells Without Myc From Mouse and Human Fibroblasts", Nature Biotechnology, 26(1): 101-106, Jan. 2008.
Office Action dated Jul. 12, 2015 From the Israel Patent Office Re. Application No. 223017 and Its Translation Into English.
Communication Pursuant to Article 94(3) EPC dated Mar. 27, 2015 From the European Patent Office Re. Application No. 10710685.8.
Communication Pursuant to Article 94(3) EPC dated Mar. 27, 2015 From the European Patent Office Re. Application No. 10712582.5.
Communication Pursuant to Article 94(3) EPC dated Mar. 27, 2015 From the European Patent Office Re. Application No. 11186963.0.
Communication Pursuant to Article 94(3) EPC dated Dec. 19, 2014 From the European Patent Office Re. Application No. 11728406.7.
Communication Pursuant to Article 94(3) EPC dated Jan. 28, 2013 From the European Patent Office Re. Application No. 10710685.8.
Communication Pursuant to Article 94(3) EPC dated Jan. 28, 2013 From the European Patent Office Re. Application No. 10712582.5.
Communication Pursuant to Rules 70(2) and 70a(2) EPC and Reference to Rule 39(1) EPC dated Mar. 4, 2013 From the European Patent Office Re. Application No. 11188963.0.
Communication Relating to the Results of the Partial International Search dated Jun. 28, 2010 From the International Searching Authority Re. Application No. PCT/IL2010/000158.
European Search Report and the European Search Opinion dated Jan. 24, 2013 From the European Patent Office Re. Application No. 11188963.0.
International Preliminary Report on Patentability dated Sep. 9, 92011 From the International Bureau of WIPO Authority Re. Application No. PCT/IL2010/000158.

(56) References Cited

OTHER PUBLICATIONS

International Preliminary Report on Patentability dated Sep. 9, 2011 From the International Bureau of WIPO Re. Application No. PCT/IL2010/000159.
International Search Report and the Written Opinion dated Oct. 11, 2010 From the International Searching Authority Re. Application No. PCT/IL2010/000158.
International Search Report and the Written Opinion dated Jun. 18, 2010 From the International Searching Authority Re. Application No. PCT/IL2010/000159.
Notice of Allowance dated Feb. 20, 2014 From the US Patent and Trademark Office Re. U.S. Appl. No. 13/203,282.
Office Action dated Oct. 7, 2013 From the Israel Patent Office Re. Application No. 214837 and Its Translation Into English.
Office Action dated Oct. 9, 2013 From the Israel Patent Office Re. Application No. 2016043 and Its Translation Into English.
Office Action dated Jan. 22, 2015 From the Israel Patent Office Re. Application No. 214837.
Office Action dated Apr. 23, 2014 From the Israel Patent Office Re. Application No. 214783 and Its Translation Into English.
Office Action dated Oct. 27, 2013 From the Israel Patent Office Re. Application No. 214783 and Its Translation Into English.
Official Action dated Aug. 8, 2013 From the US Patent and Trademark Office Re. U.S. Appl. No. 13/203,282.
Official Action dated May 16, 2013 From the US Patent and Trademark Office Re. U.S. Appl. No. 13/203,277.
Restriction Official Action dated Apr. 11, 2013 From the US Patent and Trademark Office Re. U.S. Appl. No. 13/203,282.
Restriction Official Action dated Feb. 25, 2013 From the US Patent and Trademark Office Re. U.S. Appl. No. 131203,277.
Supplemental Notice of Allowability dated Jun. 6, 2014 From the US Patent and Trademark Office Re. U.S. Appl. No. 13/203,282.
Translation Dated Feb. 9, 2015 of Office Action dated Jan. 22, 2015 From the Israel Patent Office Re. Application No. 214837.
Alison et al. "Attributes of Adult Stem Cells" The Journal of Pathology, XP002602081, 217(2): 144-160, Jan. 2009. p. 149.
Araki et al. "Chromatin-Modifying Agents Permit Human Hematopoietic Stem Cells to Undergo Multiple Cell Divisions While Retaining their Repopulating Potential", Blood, XP002583271, 109(8),: 3570-3578, Apr. 15, 2007. p. 3570-3571.
Atala et al. "Applications of Tissue Engineering in the Genetourinary Tract". Expert Review of Medical Device, 2(1): 119-126, Jan. 2005.
Balzar et al. "The Biology of the 17-1A Antigen (Ep-CAM)". The Journal of Molecular Medicine, 77: 699-712, 1999.

Boyle et al. "Fate Mapping Using Cited1-CreERT2 Mice Demonstrates That the Cap Mesenchyme Contains Self-Renewing Progenitor Cells and Gives Rise Exclusively to Nephronic Epithelia". Developmental Biology, 313: 234-245, 2008.
Brodbeck et al. "Genetic Determination of Nephrogenesis: The Pax/Eya/Six Gene Network". Pediatric and Nephrology, 19: 249-255, 2004.
Chang et al. "Contact Insensitivity of a Subpopulation of Normal Human Fetal Kidney Epithelial Cells and of Human Carcinoma Cell Lines1" Cancer Research, 47: 1634-1645, 1987.
Cirulli et al. E-Cadherin, NCAM, and Epcam Expression in Human Fetal Pancreata, Transplantation Proceedings, 27(6): 3335 Dec. 1995.
Dekel et al. "Engraftment and differentiation of Human Metanephroi Into Functional Mature Nephrons After Transplantation Into Mice is Accompanied by a Profile of Gene Expression Similar to Normal Human Kidney Development". Journla of the American Society of Nephrology, 13:997-990, 2002.
Dekel et al. "Engraftment of Human Kidney Tissue in Rat Radiation Chimera: II. Human Fetal Kidneys Display Reduced Immunogenicity to Adoptively Transferred Human Peripheral Blood Monomoclear Cells and Exhibit Rapid Growth and Development". Transplantation 64: 155-1558, 1997, Abstract.
Dekel et al. "Human and Porcine Early Kidney Precursors as a New Source for Transplantation". Nature Medicine, XP002378906 9(1): 53-60, Jan. 1, 2003.
Dekel et al. "Multiple Imprinted and Sternness Genes Provide Aa Link Between Normal and Tumor Progenitor Cells of the Developing Human Kidney". Cancer Research Xp002581965, 66(12): 6040-6049, Jun. 2006, p. 6040, Table 1.
Douville et al. "ALDH1 as a Functional Marker of Cancer Stem and Progenitor Cells", Stem Cells and Development, XP002602080, 18(1): 17-25, Jan. 2009.
Gibson D'Ambrosio et al. "Characterstics of Long-Term Human Epthelial Cell Cultures Derived From Normal Human Fetal Kidney". In Vitro Cell Development and Biology, 23(4): 279-283, Apr. 1987, Abstract.
Harari-Steinberg et al. "Identification of Human Nephron Progenitors Capable of Generation of Kidney Structures and Functional Repair of Chronic Renal Disease". EMBO Molecular Medicine, 5(1): 1556-1568, Epub Sep. 2, 2013.
Harari-Steinberg et al., "Ex Vivo Expanded 3D Human Kidney Spheres Engraft Long Term and Repair Chronic Renal Injury in Mice" Cell Rep 30, 852-869, 2020.

\* cited by examiner

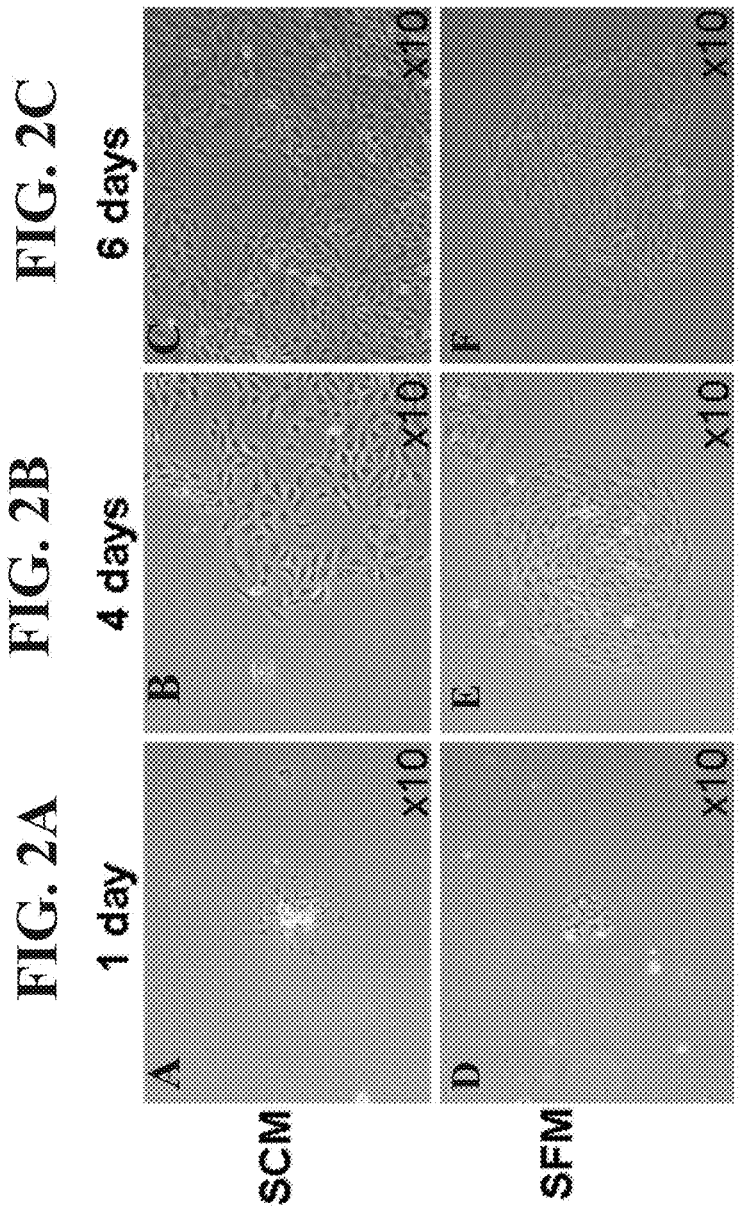

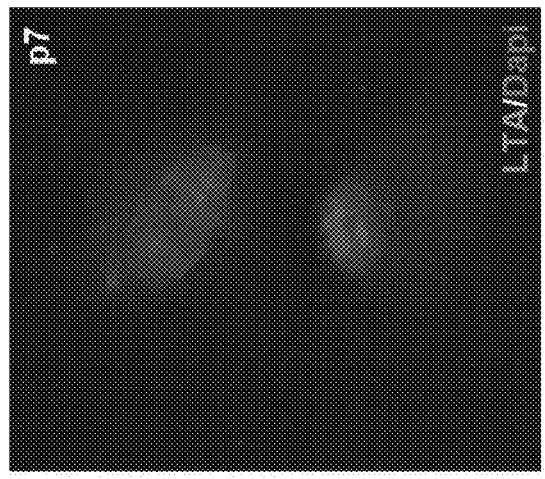
FIG. 3A FIG. 3B
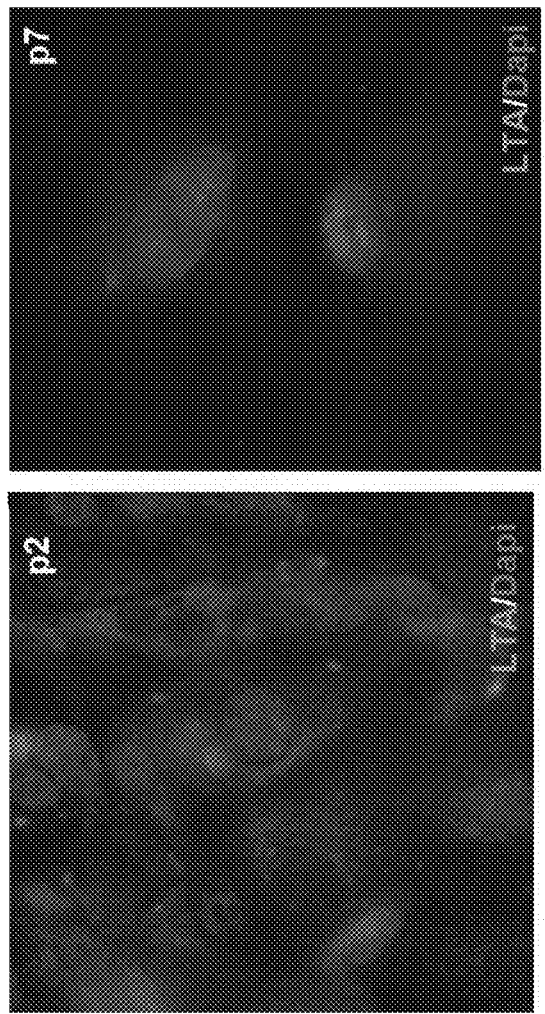
FIG. 3C
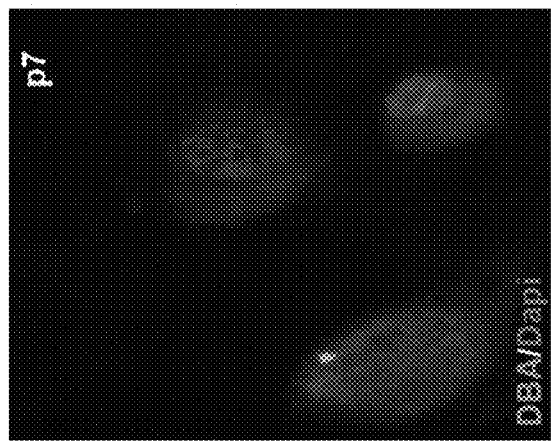
FIG. 3D
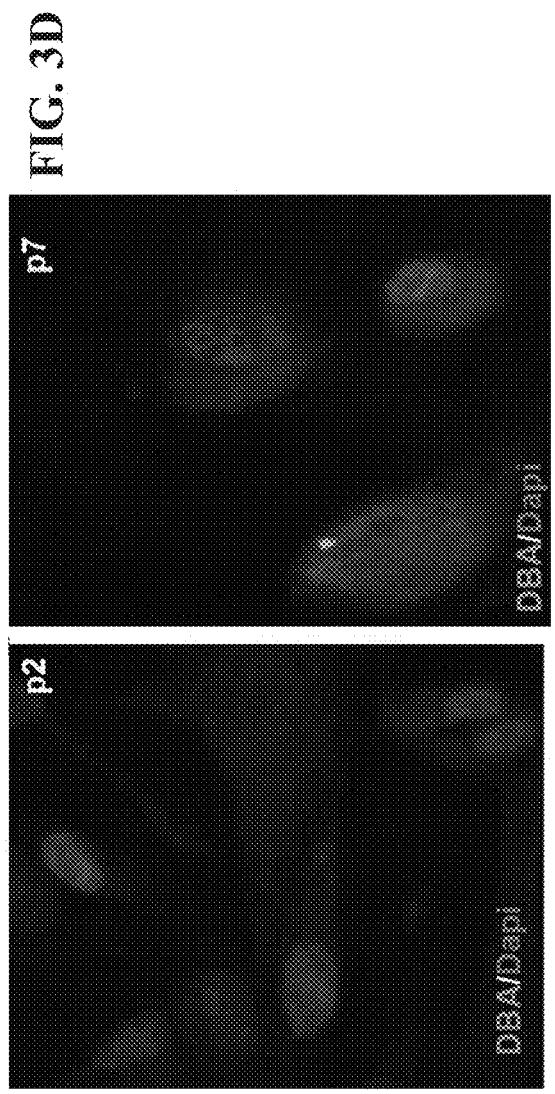

FIG. 6A
Sph P2
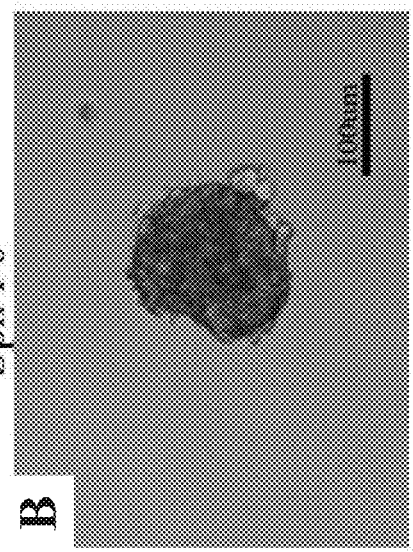
FIG. 6B
Sph P6
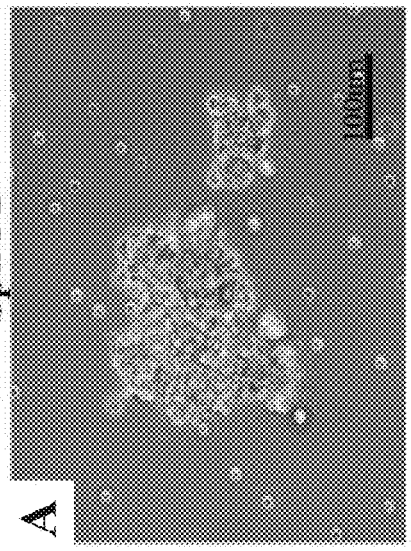
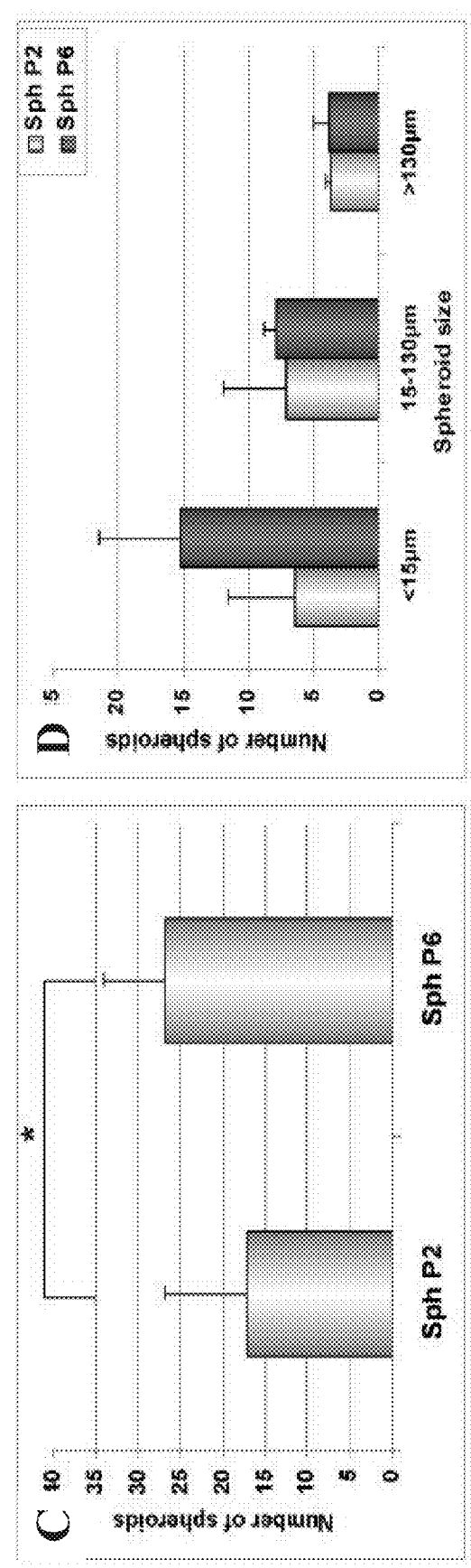
FIG. 6C
FIG. 6D

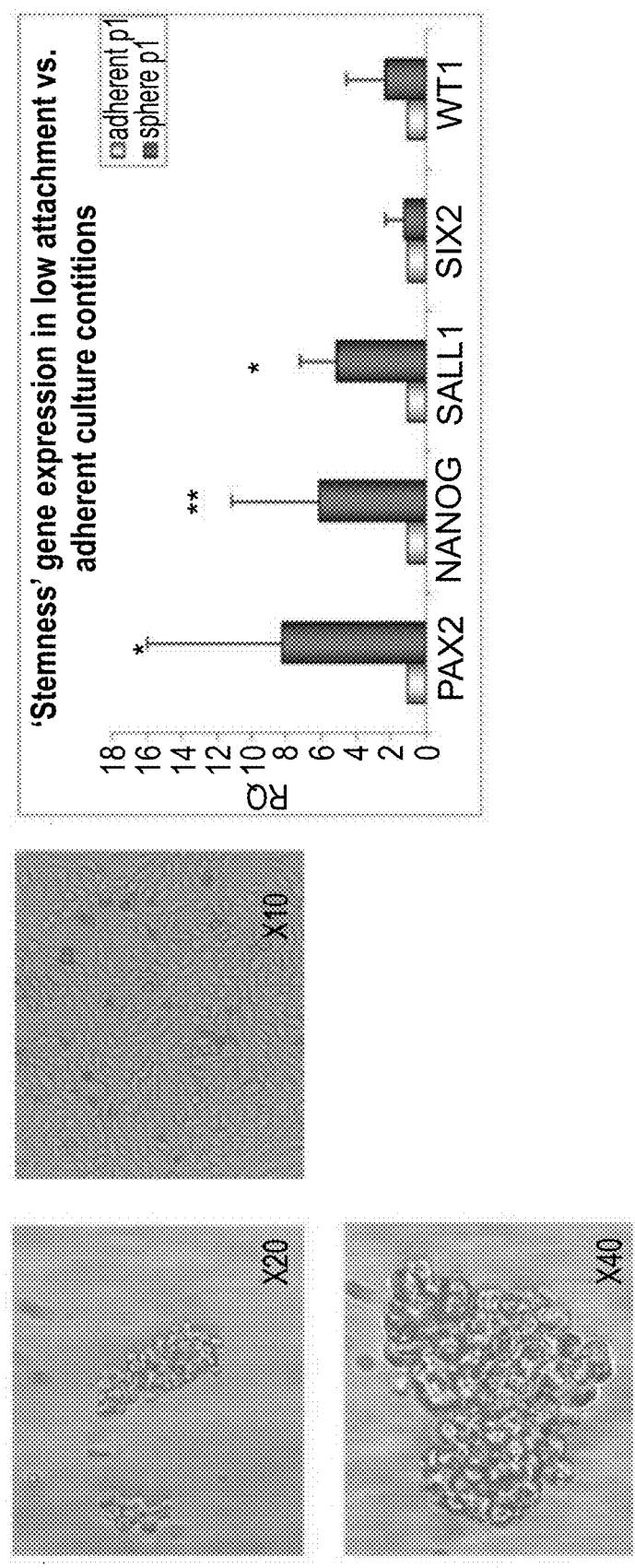

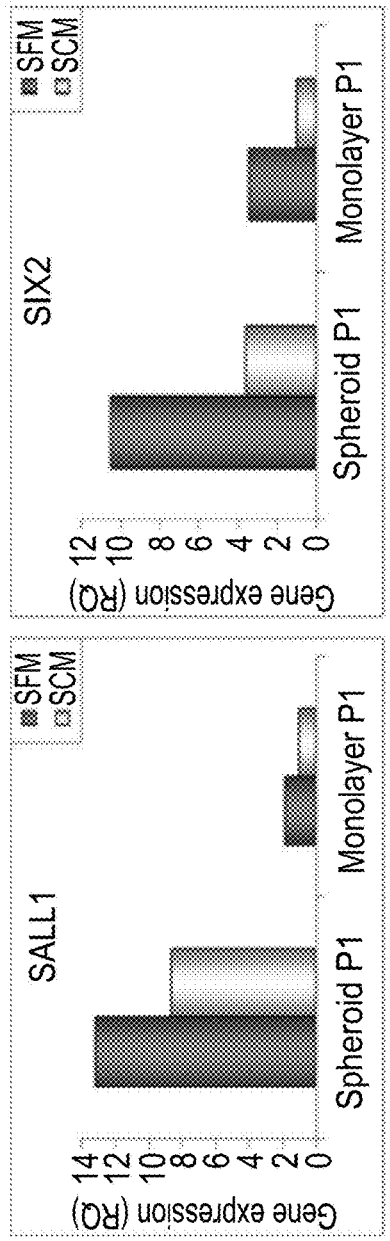
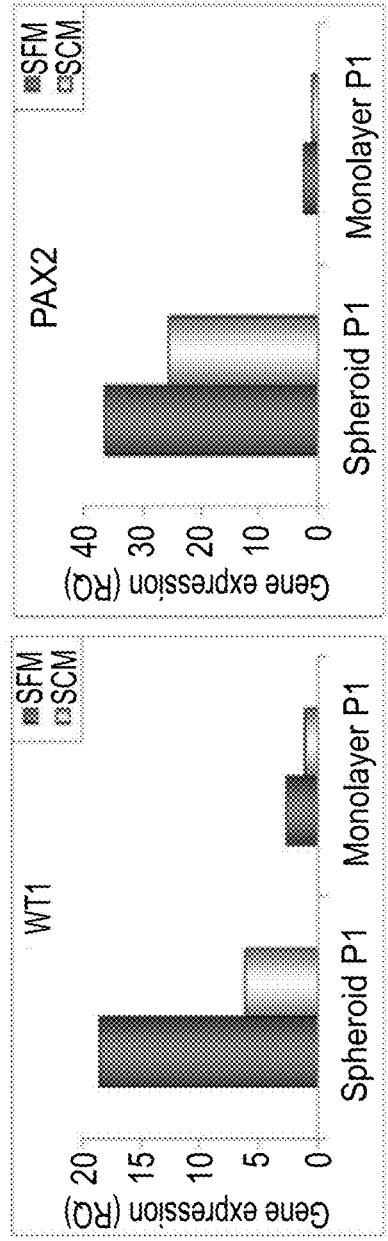
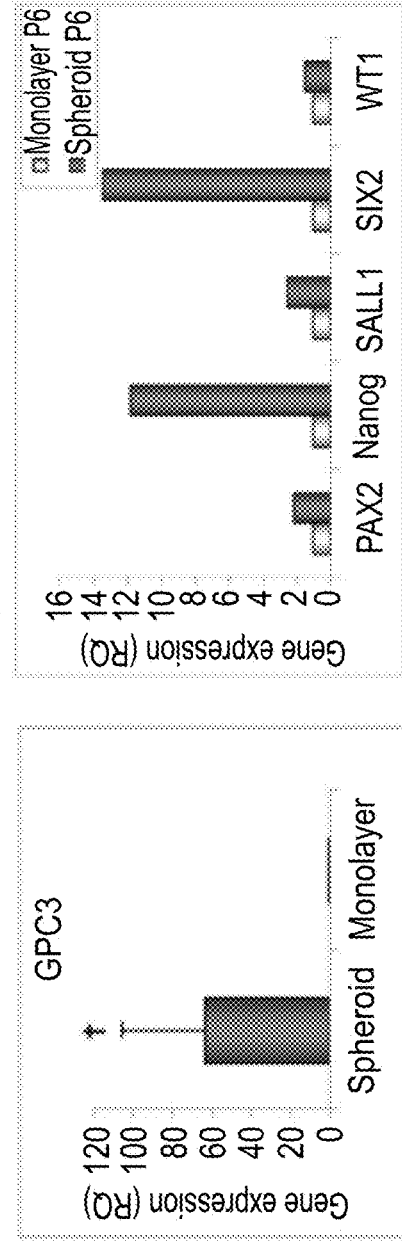
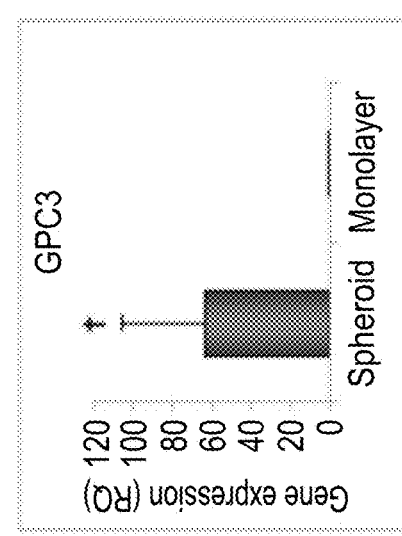
FIG. 8E  FIG. 8F  FIG. 8G  FIG. 8H  FIG. 8I  FIG. 8J

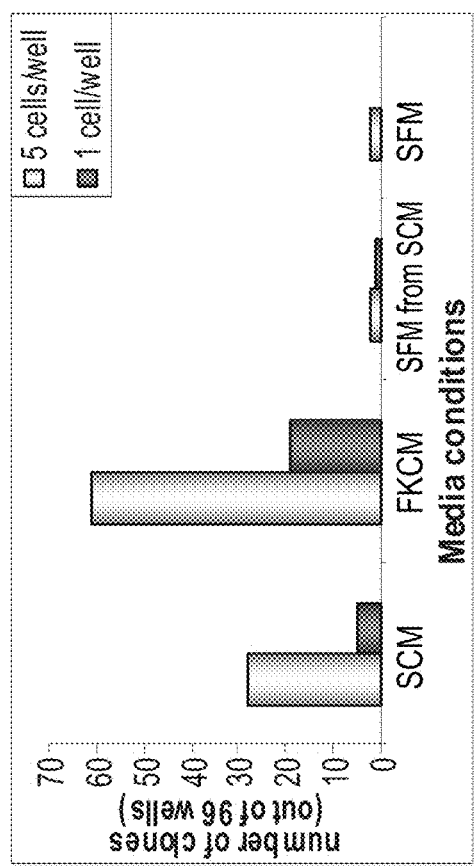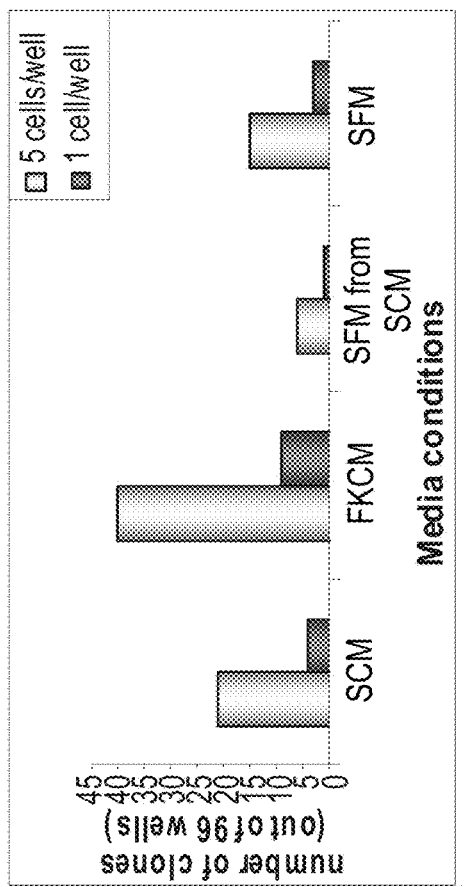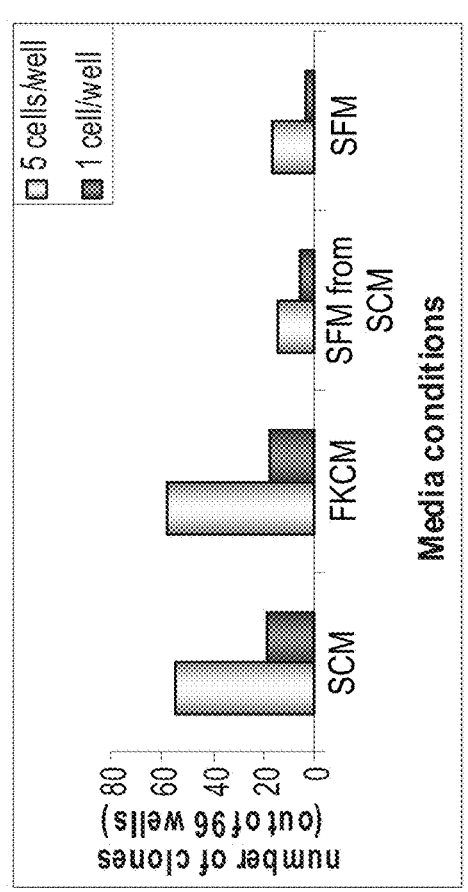

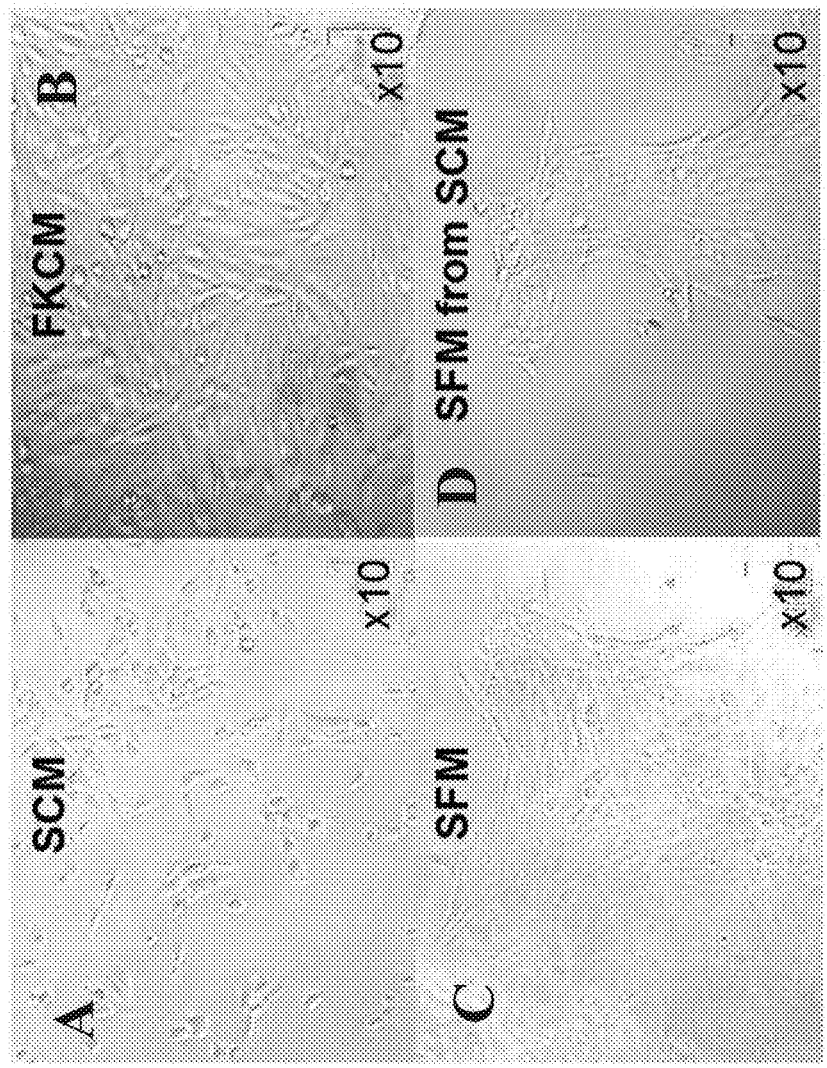

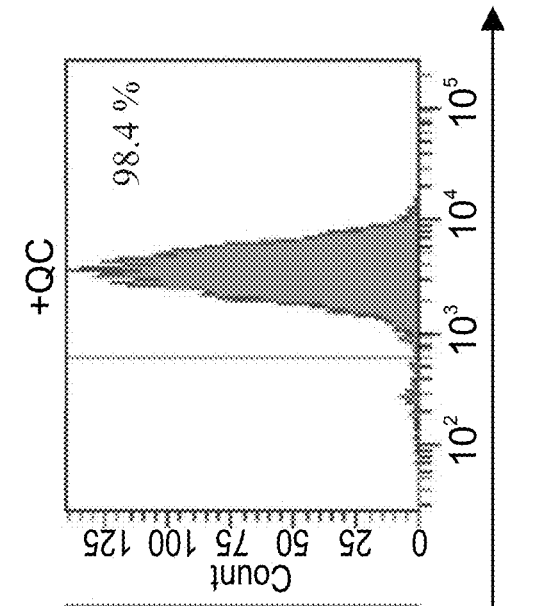
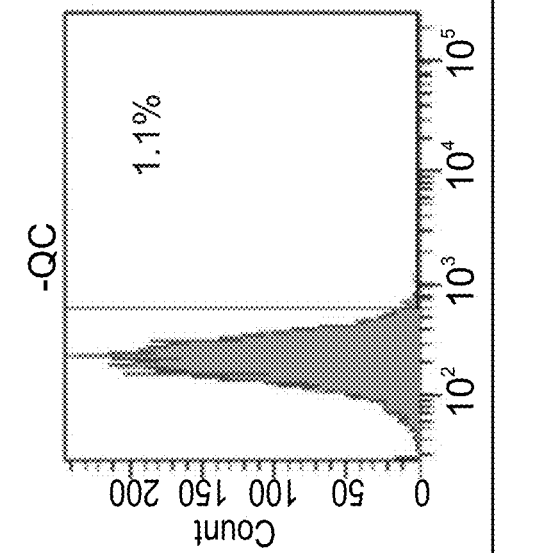
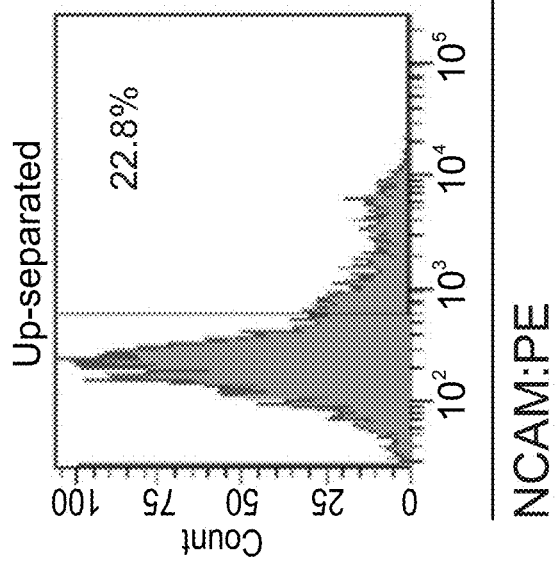
NCAM:PE

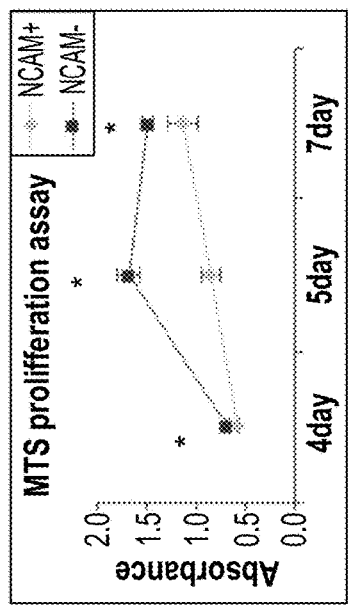
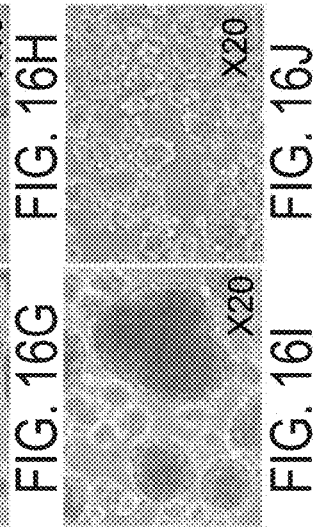
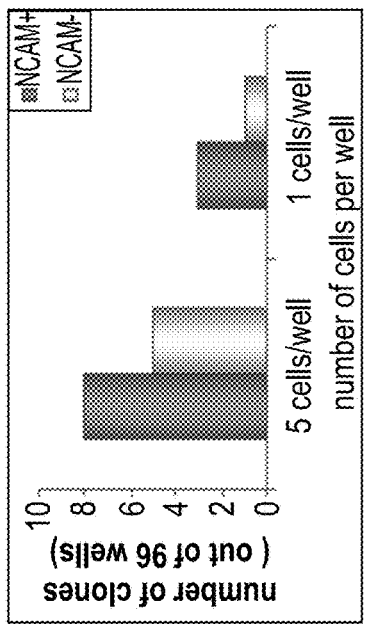
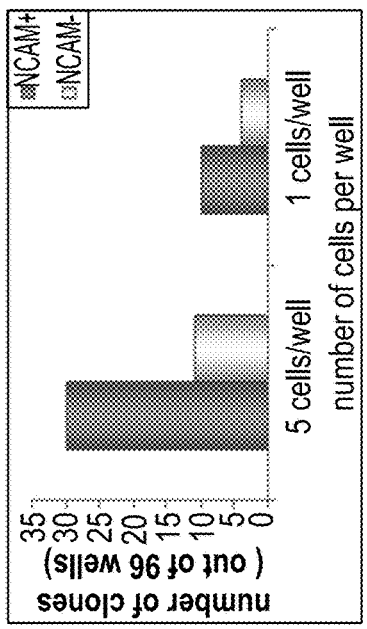
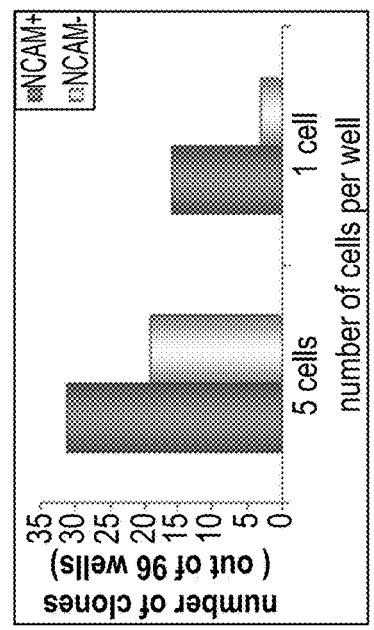
FIG. 16A FIG. 16B FIG. 16C FIG. 16D FIG. 16E FIG. 16F FIG. 16G FIG. 16H FIG. 16I FIG. 16J

Spheroids        Monolayer
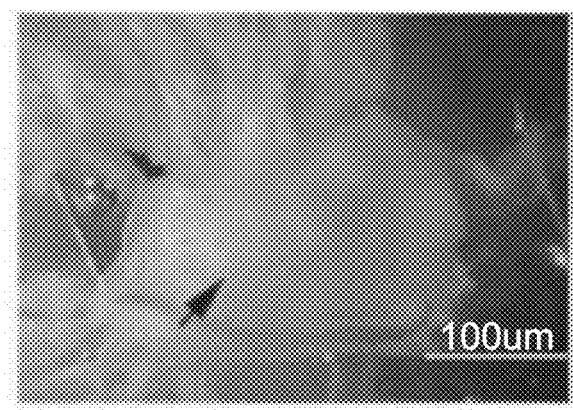 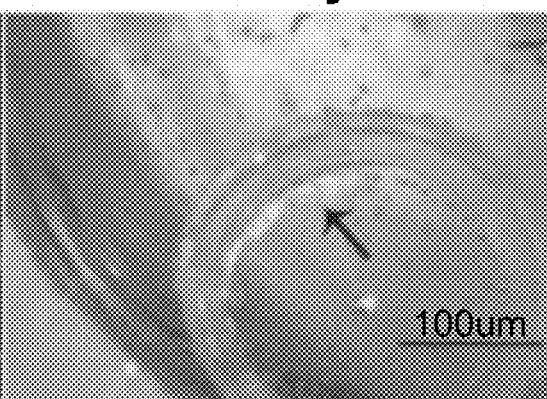
FIG. 17A        FIG. 17B
P2 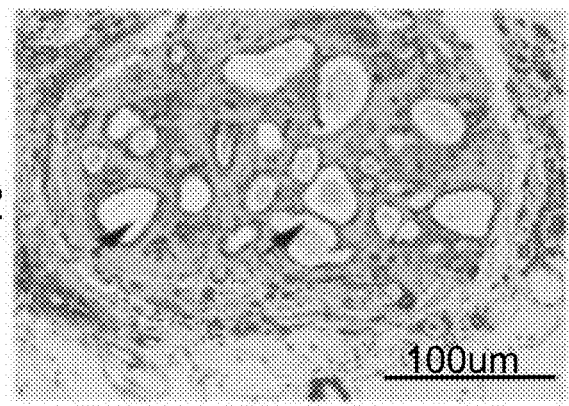 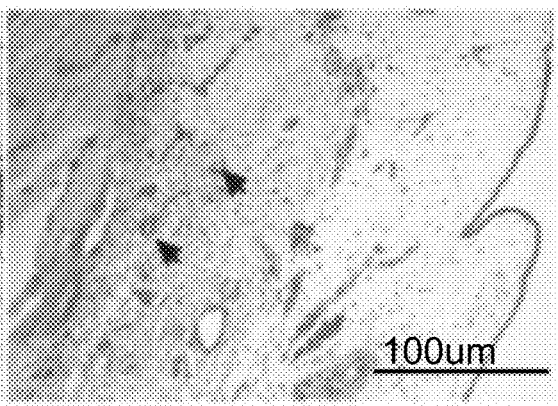
FIG. 17C        FIG. 17D
P6 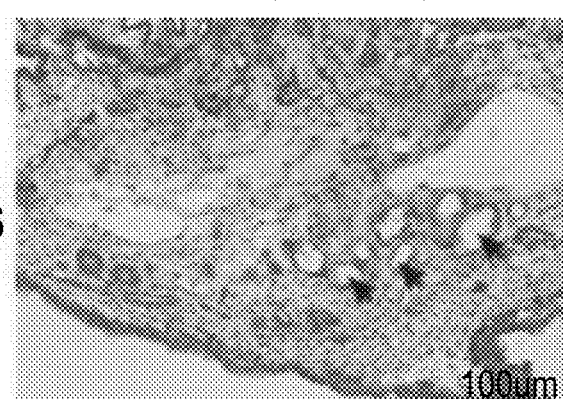 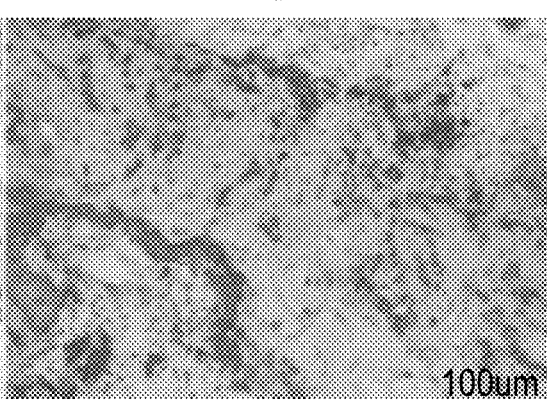
FIG. 17E        FIG. 17F

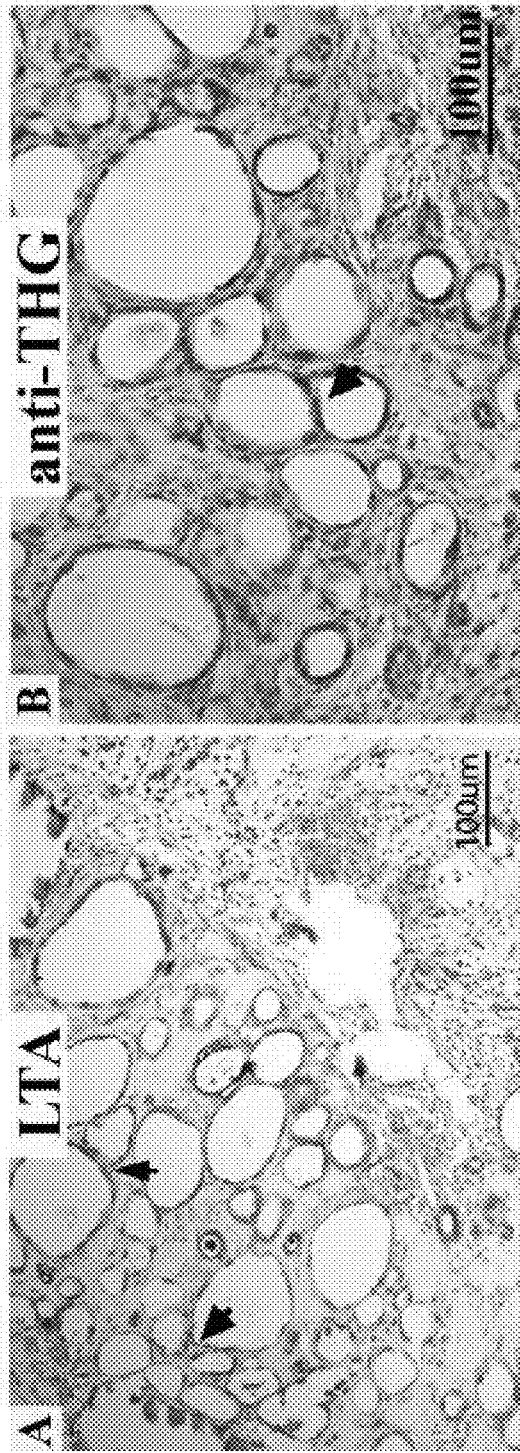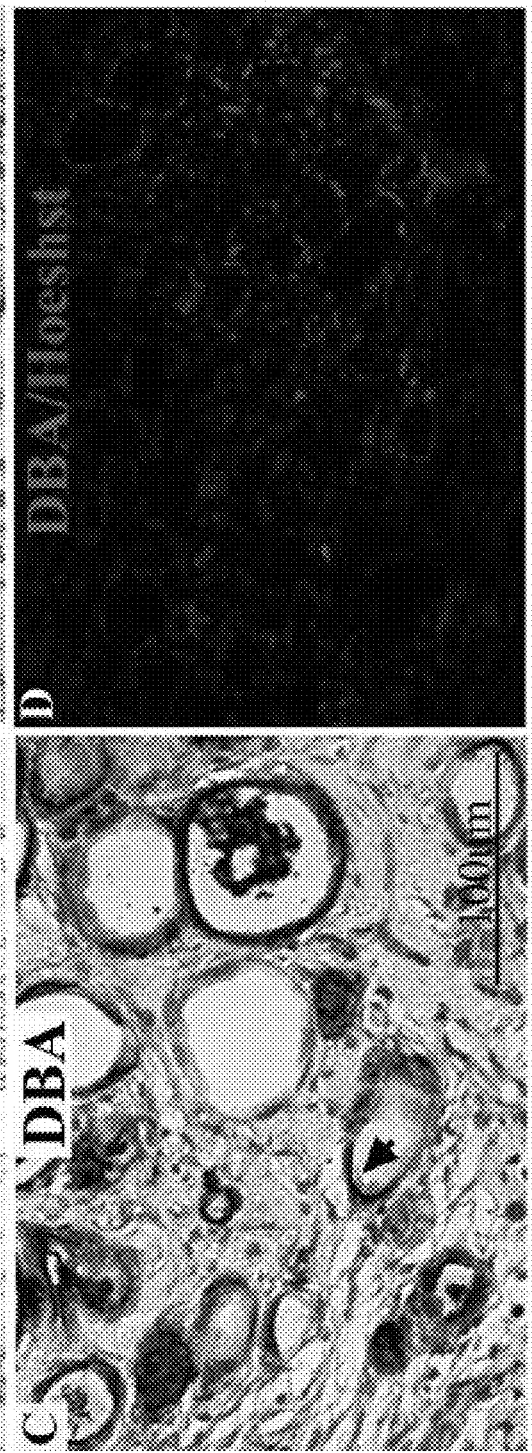
FIG. 18A  FIG. 18B  FIG. 18C  FIG. 18D

ISOLATED POPULATIONS OF ADULT RENAL CELLS AND METHODS OF ISOLATING AND USING SAME

CROSS-REFERENCE TO RELATED APPLICATIONS

This is a Division of co-pending U.S. patent application Ser. No. 13/697,531 filed Nov. 13, 2012, which is the US National Stage of International Patent Application No. PCT/IL2011/000376 filed May 12, 2011, which in turn claimed priority to U.S. Provisional Patent Application No. 61/457,613 filed May 2, 2011, and U.S. Provisional Patent Application No. 61/334,206 filed May 13, 2010. The contents of the foregoing patent applications are incorporated by reference herein in their entirety.

FIELD AND BACKGROUND OF THE INVENTION

The present invention, in some embodiments thereof, relates to isolated populations of adult renal cells and methods of isolating and using same.

The kidney is a vital organ in mammals, responsible for fluid homeostasis, waste excretion, and hormone production. There are a variety of possible injuries and disorders including cancer, trauma, infection, inflammation and iatrogenic injuries or conditions that can lead to chronic disease or cause reduction or loss of function of a kidney. The incidence of chronic kidney disease in the United States has reached epidemic proportions, and a significant number of these patients will develop end-stage renal disease (ESRD), with glomerular filtration rates too low to sustain life. Dialysis is the major treatment modality for ESRD, but it has significant limitations in terms of morbidity, mortality, and cost. Allogenic kidney transplantation provides significant benefits in terms of mortality and is ultimately less costly, but is hampered by a severe shortage of available donor organs. Acute renal failure (ARF) is also quite common, having a mortality rate that ranges from 20 to 70%. For a number of reasons, including aggressive care of an older patient population, the mortality rate due to ARF has not changed over the past 20 years despite advances in technology and therapies.

Although kidney disease has a variety of individual types, they appear to converge into a few pathways of disease progression. The functional unit of the kidney is the nephron. There is a decrease in functioning nephrons with the progression of the disease; the remaining nephrons come under more stress to compensate for the functional loss, thereby increasing the probability of more nephron loss and thus creating a vicious cycle. Furthermore, unlike tissues such as bone or glandular epithelia which retain significant capacity for regeneration, it has generally been believed that new nephron units are not produced after birth, that the ability of the highly differentiated tissues and structures of the kidneys have limited reparative powers and, therefore, that mammals possess a number of nephron units that can only decline during post-natal life. There is an increasing interest in developing novel therapies for kidney disease, including artificial organs, genetic engineering, and cell therapy.

Many adult tissues are considered to harbor cells that self-renew and differentiate to form clones of stem, progenitor, and mature cells of the organ, fitting within the criteria of tissue-specific multipotential stem cells, including the skin, the hematopoietic system and the intestine. In contrast to these rapidly-cycling organs, the kidney has a low rate of cell turnover under steady state conditions and it's regenerative capacity is limited. Extra-renal tissue-specific stem cells, including those of the bone marrow do not harbor nephrogenic potential, motivating the search for an adult kidney stem cell. To date, there is no definite evidence for the existence in the adult kidney of a cell that fits within this definition, and is capable of self-renewing and differentiating into the nephron's cell types on the one hand and on the other hand of localizing to sites of injury, thereby contributing to renal repair.

The self-renewing nephron progenitor population residing in the metanephric mesenchyme (MM) and more specifically in the condensed mesenchyme (CM) is entirely exhausted with the completion of nephrogenesis (human-$34^{th}$ gestational week, mice-2 weeks postnatal) and therefore no progenitor population with similar nephrogenic potential to the MM/CM exists in the adult kidney (6, 7). However, a population may exist with a more restricted potential than the CM (for instance a progenitor cell type for proximal tubular cells). This cell type is likely to arise from within the epithelial tubular compartment as Humphreys et al (8) demonstrated by lineage tracing that the cells responsible for tubular repopulation after kidney ischemia are of tubular origin, thereby excluding an extra-tubular source.

Murine studies have elucidated early markers specifying the epithelial renal progenitor population including a unique combination of transcription factors such as Hox11 paralogs, Osr1, Pax2, Eya1, Wt1, Sall1, Six2, and Cited1 (9). These early renal progenitor markers have been mostly shown to down-regulate with cessation of nephrogenesis in both murine (6) and human kidneys (7).

International PCT Application IL2010/000158 teaches isolation and characterization of fetal renal progenitor cells.

Bussolati et al [American Journal of Pathology. 2005; 166:545-555] teaches isolation and characterization of CD133+ cells derived from normal adult human kidney and suggest that this cell population represent a multipotent adult resident stem cell population that may contribute to the repair of renal injury.

SUMMARY OF THE INVENTION

According to an aspect of some embodiments of the present invention there is provided an isolated cell population of human adult kidney cells, comprising at least 80% adult renal stem cells having a NCAM+ signature.

According to an aspect of some embodiments of the present invention there is provided a method of isolating human adult renal cells comprising enriching for a subpopulation of renal cells from an adult renal tissue, the subpopulation of renal cells having a NCAM+ signature, wherein the enriching is effected such that at least 80% of the adult renal cells are of the subpopulation of renal cells.

According to an aspect of some embodiments of the present invention there is provided a method of determining clonogenic potential of an adult renal cell population, the method comprising:

(a) culturing the adult renal cell population in serum-comprising medium and conditioned medium from human fetal kidney cells; and (b) counting a number of clones formed from the adult renal cells of the population, thereby determining clonogenic potential of an adult renal cell population.

According to an aspect of some embodiments of the present invention there is provided a cell culture comprising a culture medium and the isolated cell population comprising at least 80% adult renal stem cells having a NCAM+ signature.

According to an aspect of some embodiments of the present invention there is provided a method of treating a renal damage in a subject in need thereof comprising administering to the damaged kidney of the subject a therapeutically effective amount of the isolated cell population comprising at least 80% adult renal stem cells having a NCAM+ signature, thereby treating the renal disease in the subject.

According to an aspect of some embodiments of the present invention there is provided a method of identifying an agent capable of regulating differentiation of a renal stem cell, the method comprising contacting the isolated population of cells comprising at least 80% adult renal stem cells having a NCAM+ signature with an agent, wherein a change in developmental phenotype is indicative of the agent capable of regulating differentiation of the renal stem cells.

According to an aspect of some embodiments of the present invention there is provided a method of generating a nephrospheroid, the method comprising culturing human adult kidney cells in a culture medium under non-adherent conditions, thereby generating the nephrospheroid.

According to an aspect of some embodiments of the present invention there is provided an isolated nephrospheroid comprising human adult kidney cells.

According to an aspect of some embodiments of the present invention there is provided a cell culture comprising a culture medium and an isolated population of nephrospheroids, the nephrospheroids comprising human adult kidney cells.

According to an aspect of some embodiments of the present invention there is provided a method of identifying an agent capable of regulating differentiation of a renal stem cell, the method comprising contacting an isolated population of nephrospheroids with an agent, the nephrospheroids comprising human adult kidney cells, wherein a change in developmental phenotype is indicative of the agent capable of regulating differentiation of the renal stem cells.

According to an aspect of some embodiments of the present invention there is provided a method of treating a renal damage in a subject in need thereof comprising administering to the damaged kidney of the subject a therapeutically effective amount of an isolated population of nephrospheroids, the nephrospheroids comprising human adult renal cells, thereby treating the renal disease in the subject.

According to some embodiments of the invention, the enriching is effected by detecting surface marker expression of NCAM.

According to some embodiments of the invention, the cells are seeded on a scaffold.

According to some embodiments of the invention, the method further comprises dispersing the human adult kidney cells prior to culturing.

According to some embodiments of the invention, the medium further comprises epidermal growth factor (EGF) and fibroblast growth factor (FGF).

According to some embodiments of the invention, the medium further comprises insulin and progesterone.

According to some embodiments of the invention, the medium is devoid of serum.

According to some embodiments of the invention, the medium comprises serum.

According to some embodiments of the invention, the method further comprises expanding human adult kidney cells in a culture medium under adherent conditions prior to the culturing.

According to some embodiments of the invention, the culture medium comprises serum.

According to some embodiments of the invention, the isolated nephrospheroid is characterized by enhanced expression of at least one polypeptide selected from the group consisting of sal1, pax2, six2 and WT1 as compared to the adult kidney cells grown under adherent conditions.

According to some embodiments of the invention, the isolated nephrospheroid is characterized by enhanced expression of each of sal1, pax2, six2 and WT1 as compared to the adult kidney cells grown under adherent conditions According to some embodiments of the invention, the isolated nephrospheroid is generated in a serum-free medium.

According to some embodiments of the invention, the isolated nephrospheroid is generated in serum-containing medium.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
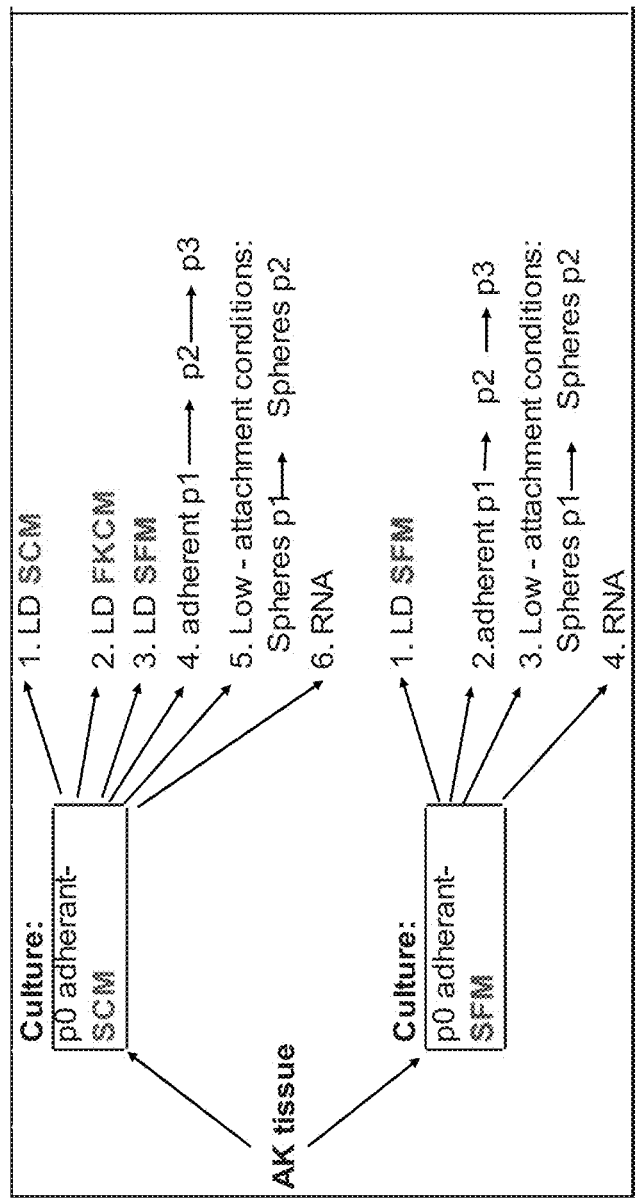
Figures 3E, 3F, 3G, 3H, 3I, 3J:
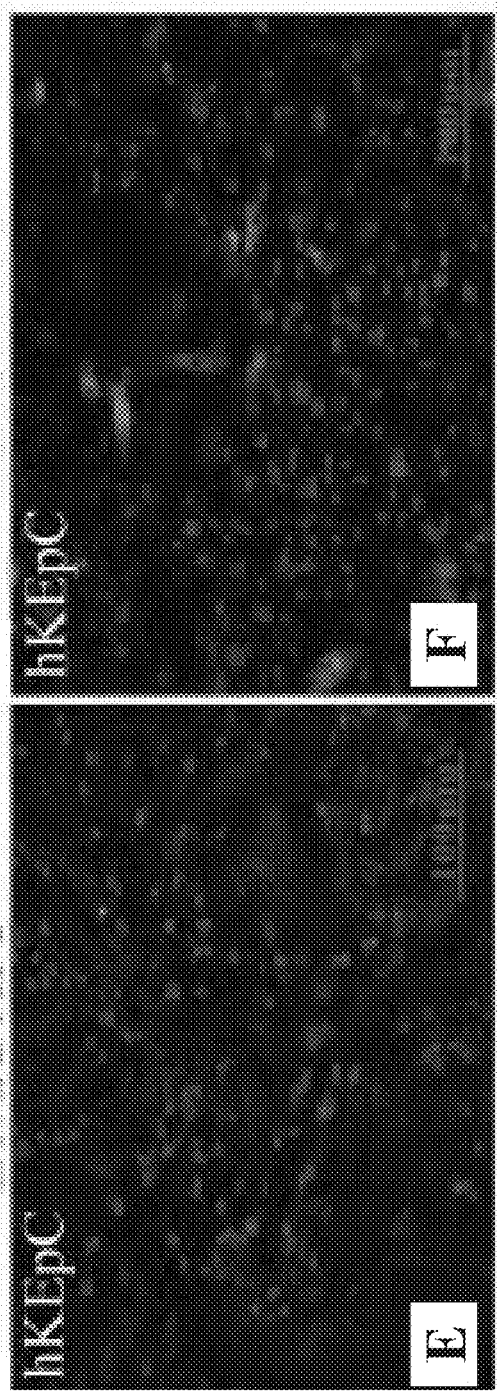
Figures 4A, 4B, 4C, 4D, 4E, 4F:
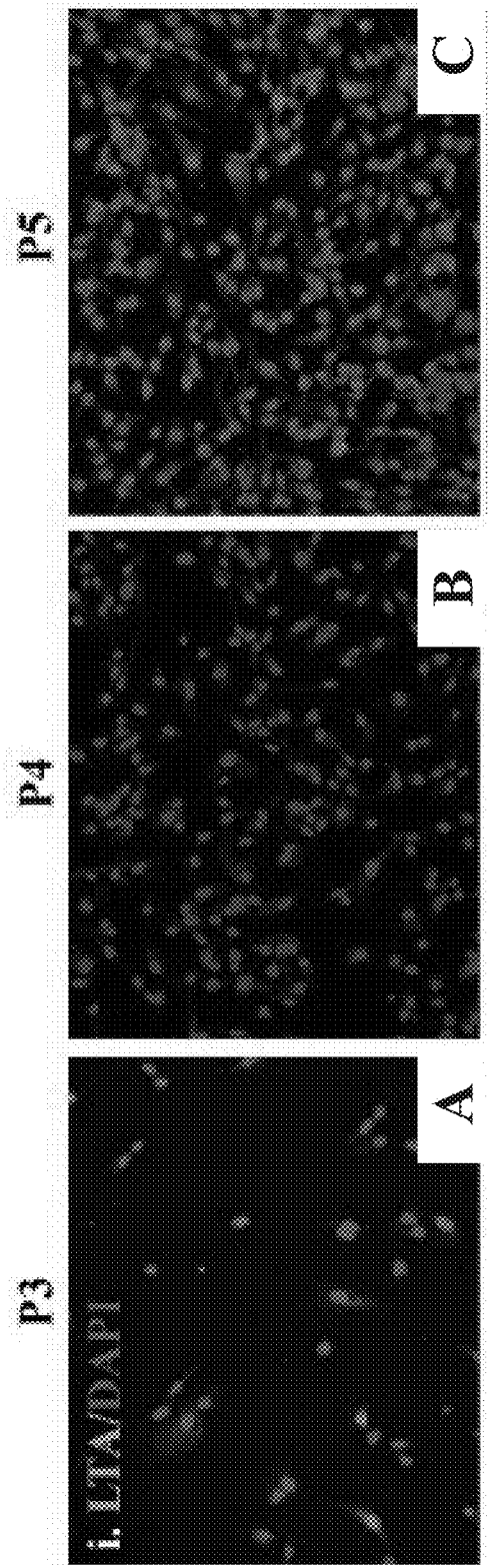
Figures 5A, 5B, 5C, 5D, 5E:
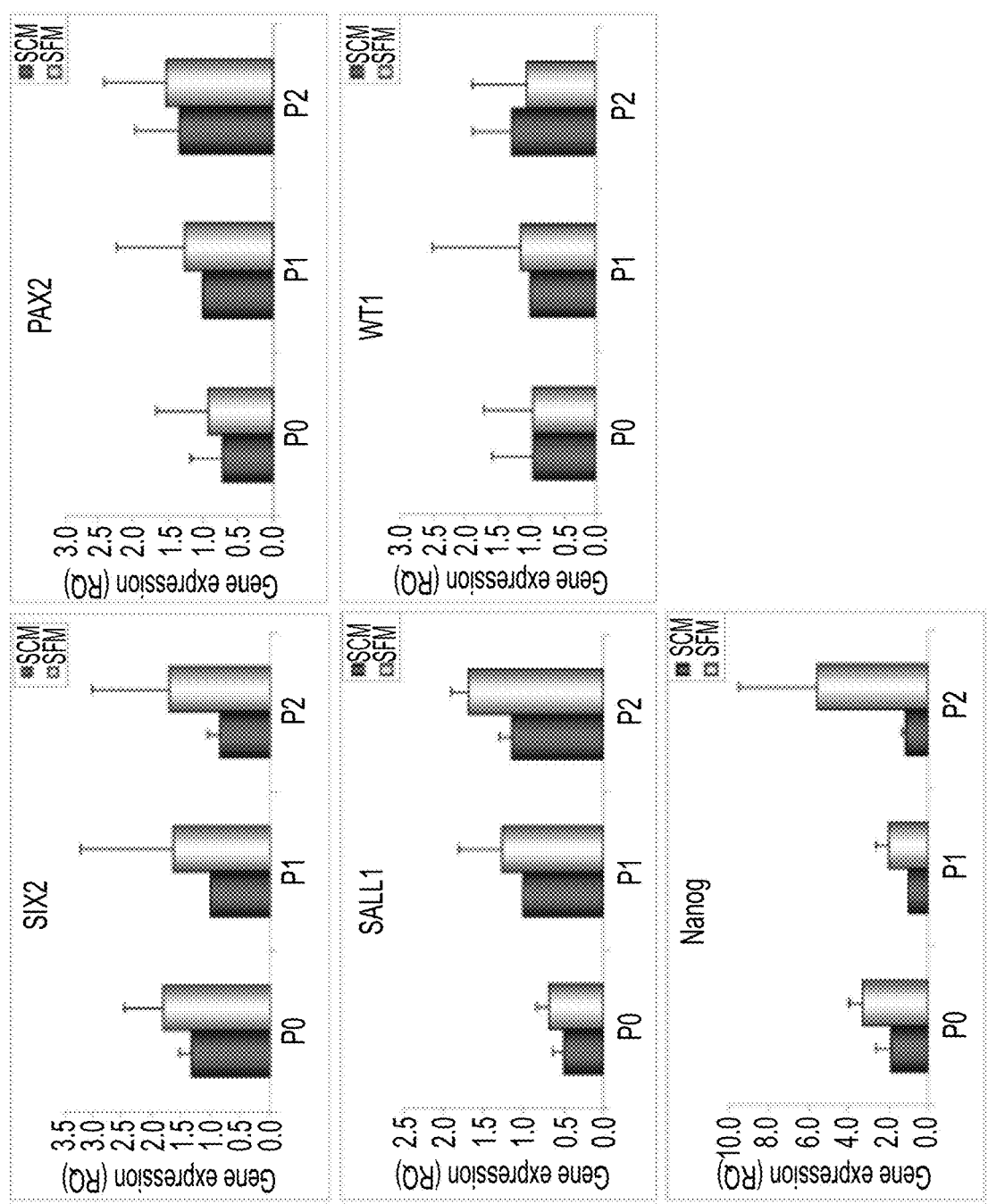

FIG. 1 is a diagram of the experimental design for ascertaining culture conditions for isolation of adult renal progenitor cells. Adult kidney tissues were collected from patients nephrectomized due to localized renal tumors. The tissues were digested to a single cell suspension. Cells were grown using either in Serum containing media (SCM) or Serum-free media (SFM). Upon receiving confluent adherent culture (after approximately 7 days), cells were harvested and subjected to limiting dilutions, RNA extraction, sphere formation and continuous adherent culture assays. FKCM—Fetal kidney conditioned media, LD—Limiting Dilution.

FIGS. 2A-F are photographs illustrating the growth pattern of hAK cells in two different growth media: SCM and SFM. After one day in culture only a few cells adhered, a few days later these cells started to expand, demonstrating a different pattern of expansion; in SFM expansion was concentric and defined, whereas in SCM, expansion was in less organized manner.

FIGS. 3A-J are photographs illustrating adult kidney cell culture characteristics. In low-passage cultures (passage 1) there is a predominance of proximal tubular cells, indicated by LTA staining and a minority of collecting duct' cells, indicated by DBA staining. While hKEpCs positively stain for markers, negative staining is seen in human foreskin fibroblasts (HFF). As expected, renal proximal tubular epithelial cells (RPTEC) exclusively stain for LTA. Positively stained cells are green. Nuclei are stained with DAPI (blue).

FIGS. 4A-F are photographs illustrating adult kidney cell culture characteristics at passages P3-P5. The cells positively stain for both markers along the represented passages. Nuclei are stained with DAPI (blue).

FIGS. 5A-E are bar graphs illustrating the results of the qRT-PCR analysis of renal stem/progenitor genes (SAL1, SIX2, WT1 and PAX2) and pluripotency gene Nanog in SCM and SFM expanded hKEpC cultures of passages P0-P2. The values for SCM monolayer culture P1 were sued to normalize (therefore equal 1) and all other values were calculated with respect to them. Results are presented as the mean+/−SDEV of 3 separate experiments using cells from different donors.

FIGS. 6A-D are graphs and photographs illustrating the formation of hKEpC spheroids. (FIGS. 6A and B) Representative micrographs of p2 and p6 spheroid morphology (Sph P2 and Sph P6 respectively) obtained from the same hKEpC origin. While P2 spheroids are less organized, P6 spheroids are more condensed, well organixed and demonstrate true sphere morphology. (FIGS. 6C and D) Quantitative representation of P2 vs. P6 spheroid formation from $2 \times 10^4$ cells/2 ml. FIG. 6C represents spheroid number formed, showing significantly higher spheroid formation at P6. FIG. 6D represents the number of spheroids formed according to spheroid size, showing that the small size spheroids (less than 15 μm), rather than the bigger ones (more than 15 μm) predominantly contribute to the number difference between the P2 vs. P6 spheroids (represented in FIG. 6C). Graphs represent mean values from the tripicates from 3 different tissue donors.

Figure 7:
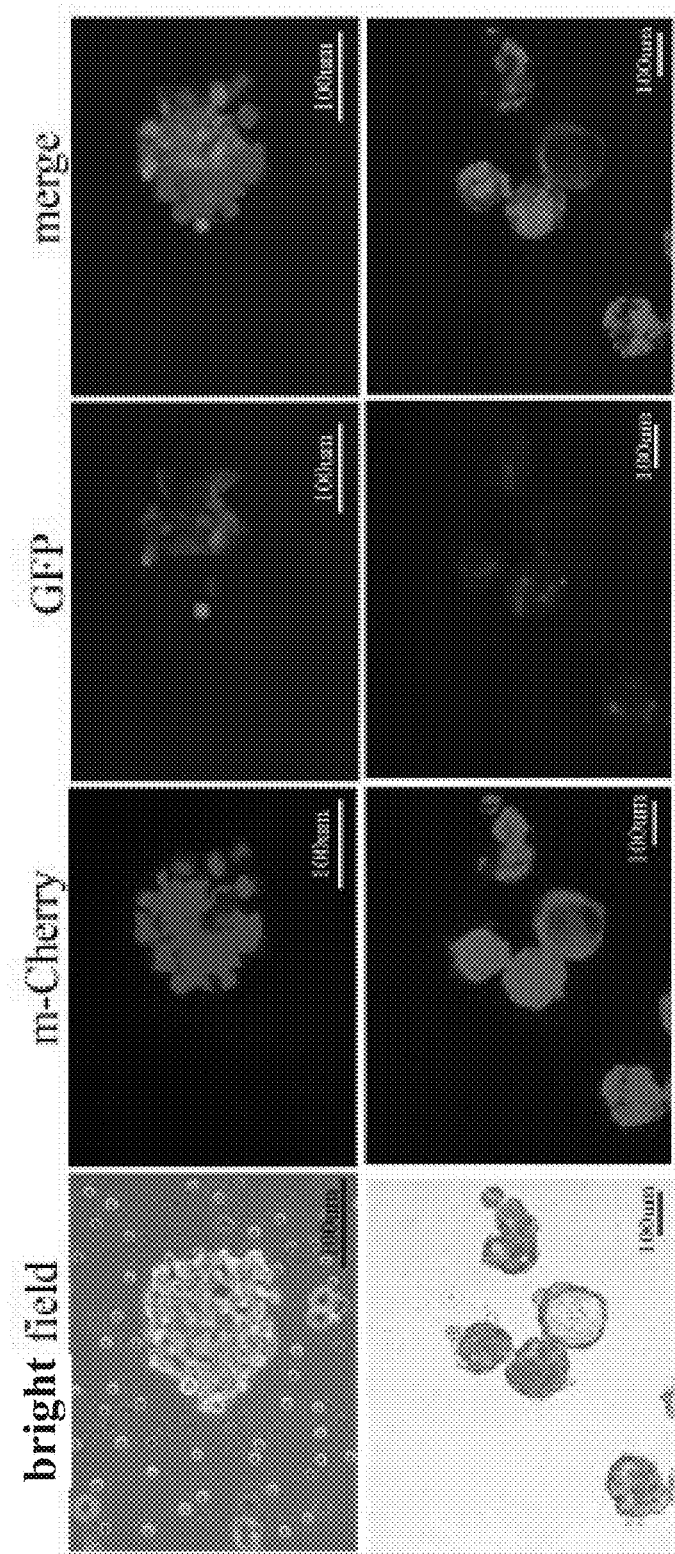

FIG. 7 are photographs illustrating the characterization of hKEpC spheroid origin. hKEpC cells grown as a monolayer were infected by lenitvirus-based vectors, carrying the gene for either green fluorescent protein (GFP, green) or m-cherry (red). Fluorescent cells were mixed at an exact ratio of 1:1 and subjected to low-attachment conditions to allow formation of spheroids. Upper panel: spheroid formation after 7 days in culture (×20). Lower panel: spheroid formation after 6 weeks in culture (×10). Images were taken by Nikon Eclipse TS100 microscope, show abundant m-cherry7 and some GFP expression, indication that at least some cell aggregation had occurred.

FIGS. 8A-J are photographs and graphs illustrating that low attachment conditions induce higher expression of renal progenitor genes. FIGS. 8A-B. Spheroid-like structures formed in the low attachment conditions from hAK cells. FIG. 8C. Adherent hAK culture; FIG. 8D. Relative quantification RT-PCR analysis shows higher nanog and fetal kidney progenitor genes expression in the low-attachment conditions (originated from adherent grown in SCM) in comparison to the adherent culture of the p1 hAK cells in SCM. *, $p<0.05$; **, $p<0.05$ after logarithmic transformation; FIG. 8E-H. Relative quantification RT-PCR analysis shows spheroids generated from adherent culture grown in SFM has higher expression of progenitor genes relative to adherent culture of hAK cell in both SFM and SCM. Mean of 3 different experiments on 3 different hAK tissues. FIG. 8I. Elevated transcript levels of Gpc3, in P1 spheroid cells (generated after expansion as a monolayer in SCM) compared to P1 monolayer culture expanded in SCM. P is less than 0.05 after logarithmic transformation. FIG. 8J. Elevated progenitor and pluripotency genes transcript levels of P6 spheroid cells (generated after expansion as a monolayer in SCM) compared to P6 monolayer culture expanded in SCM. SCM-serum containing medium. SFM—serum free medium.

Figure 9A:
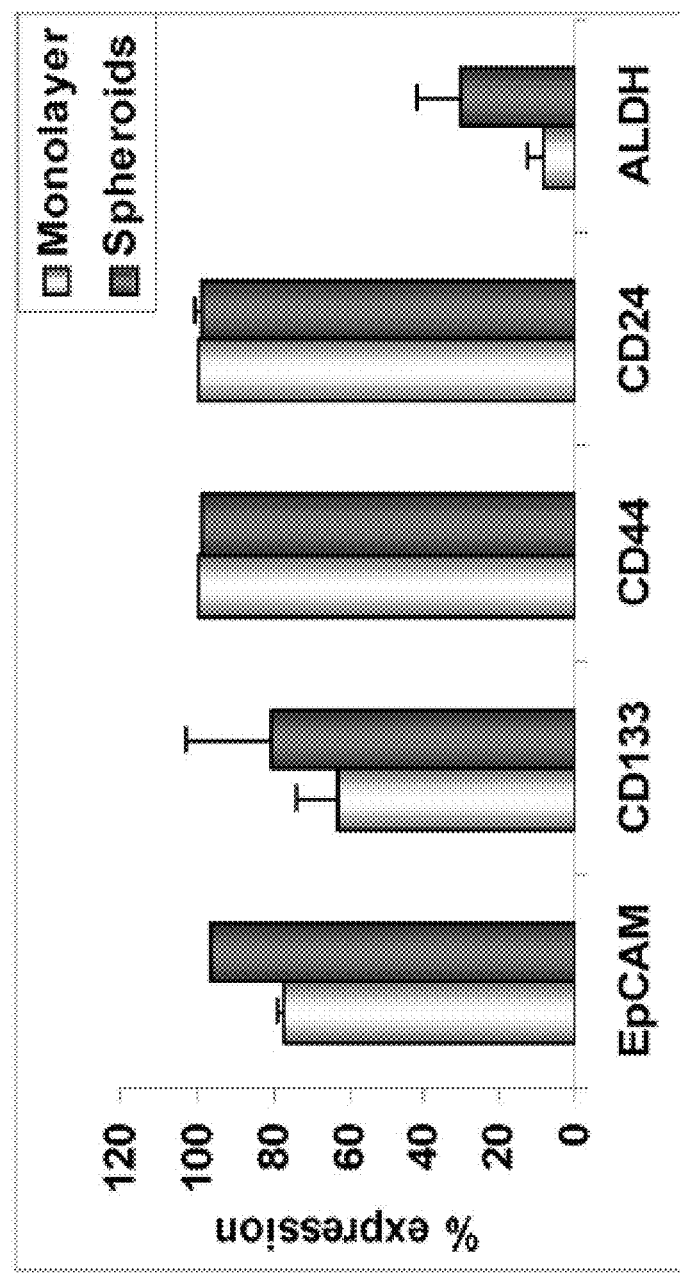

FIG. 9A is a bar graph illustrating surface marker expression and ALDH activity in spheroids vs adherent culture. Spheroids have enchanced ALDH activity in comparison to adherent culture of hAK cells. Epithelial (EpCAM, CD24), mesenchymal cell (CD44) markers and CD133 has no difference in both culture conditions.

Figure 9B:
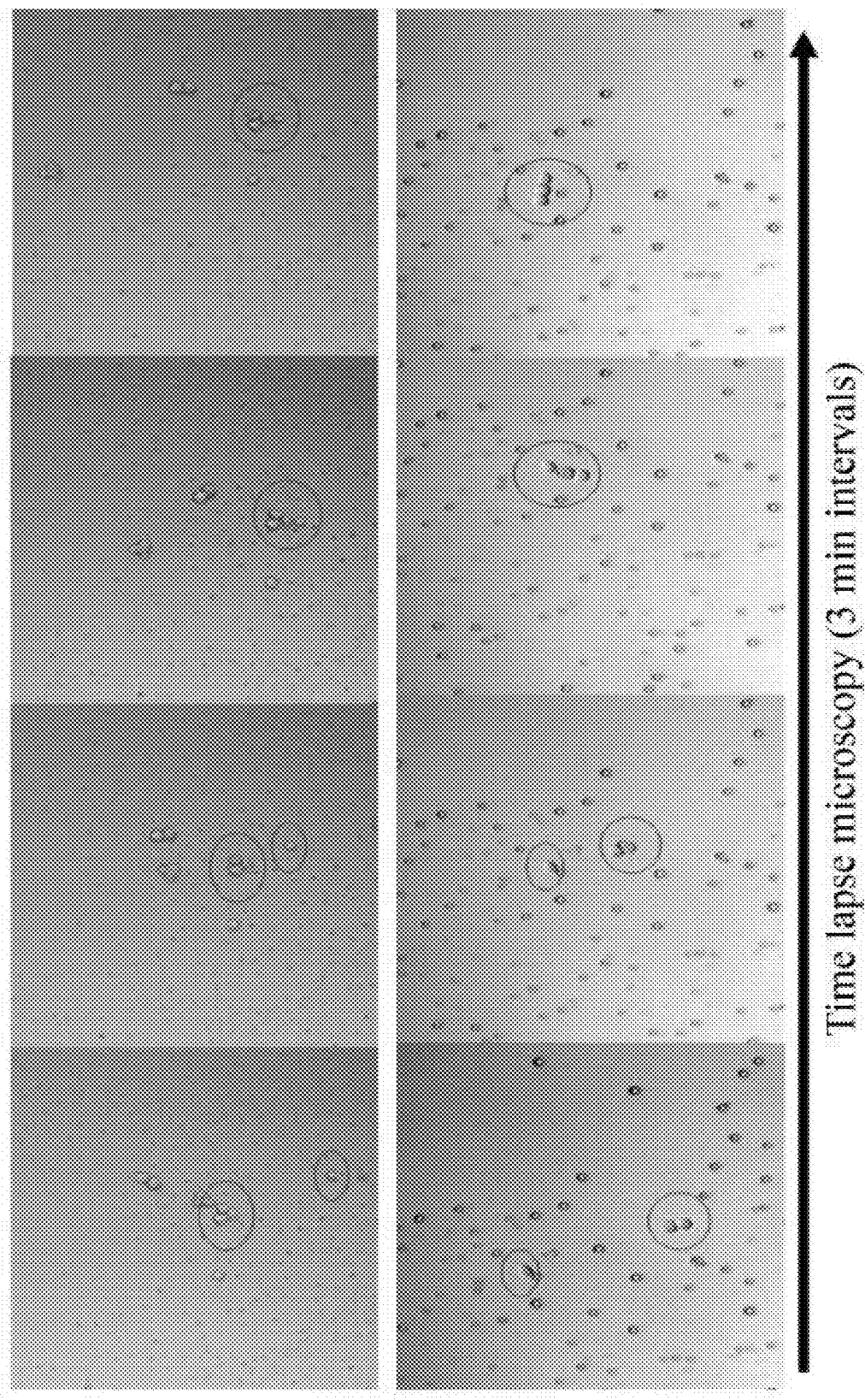

FIG. 9B are time lapse microscopy photographs of the spheroid formation. hKEpC suspension was seeded on the PolyHEMA precoated plates. Micrographs were taken by the CSN 410 Zeiss microscope (×10) with 3 minute intervals. Upper and lower planes show two representative events of cell collisions and aggregation in the process of spheroid formation.

Figure 9C:
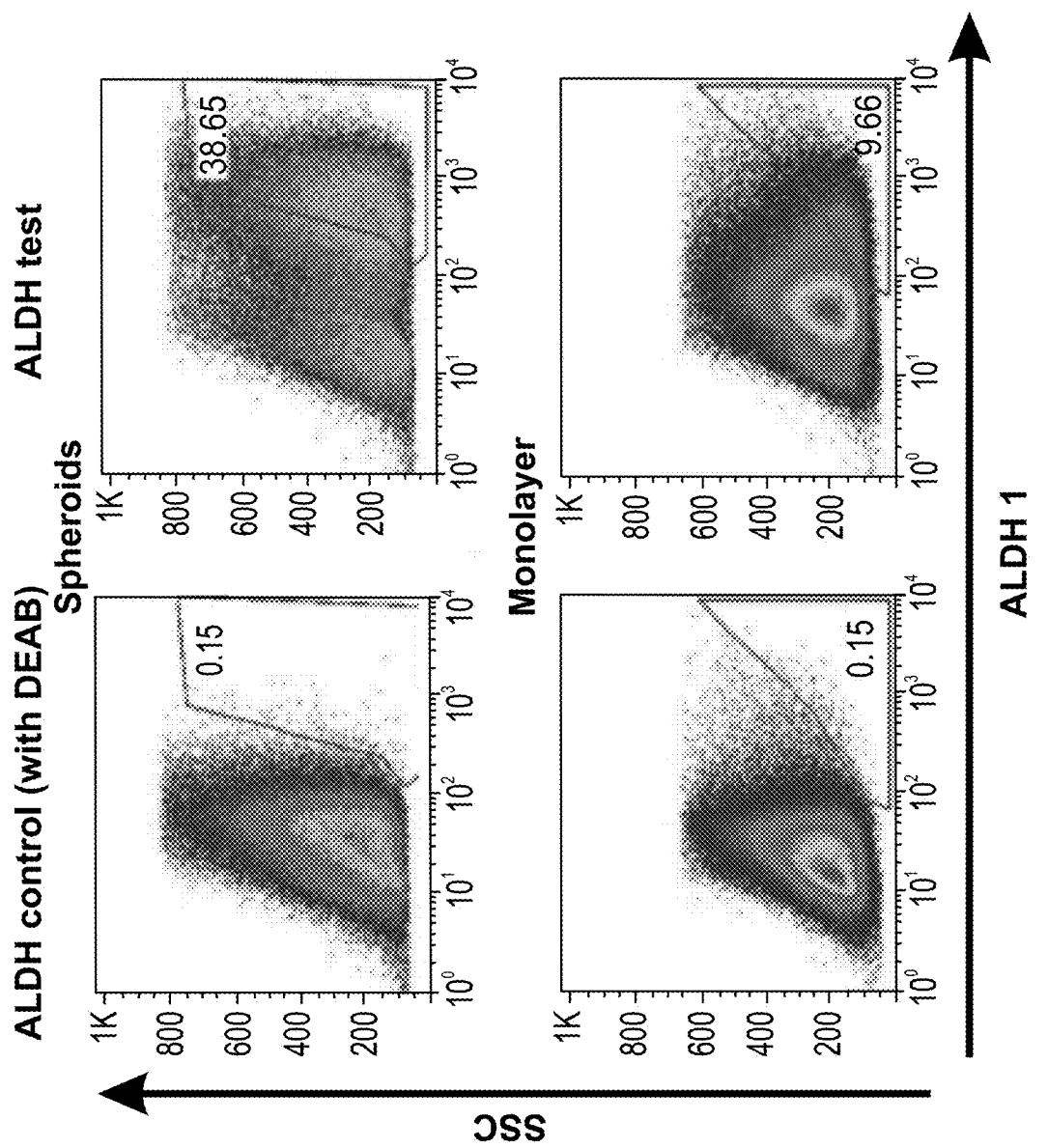

FIG. 9C are representative dot plots showing enhanced ALDH1 activity in spheoids compared to monolayer culture. ALDH1 enzymatic activity was detected using ALDE-FLUOR assay. DEAB was used to inhibit the reaction of ALDH with the ALDEFLUOR reagent, providing a negative control.

Figure 10A:
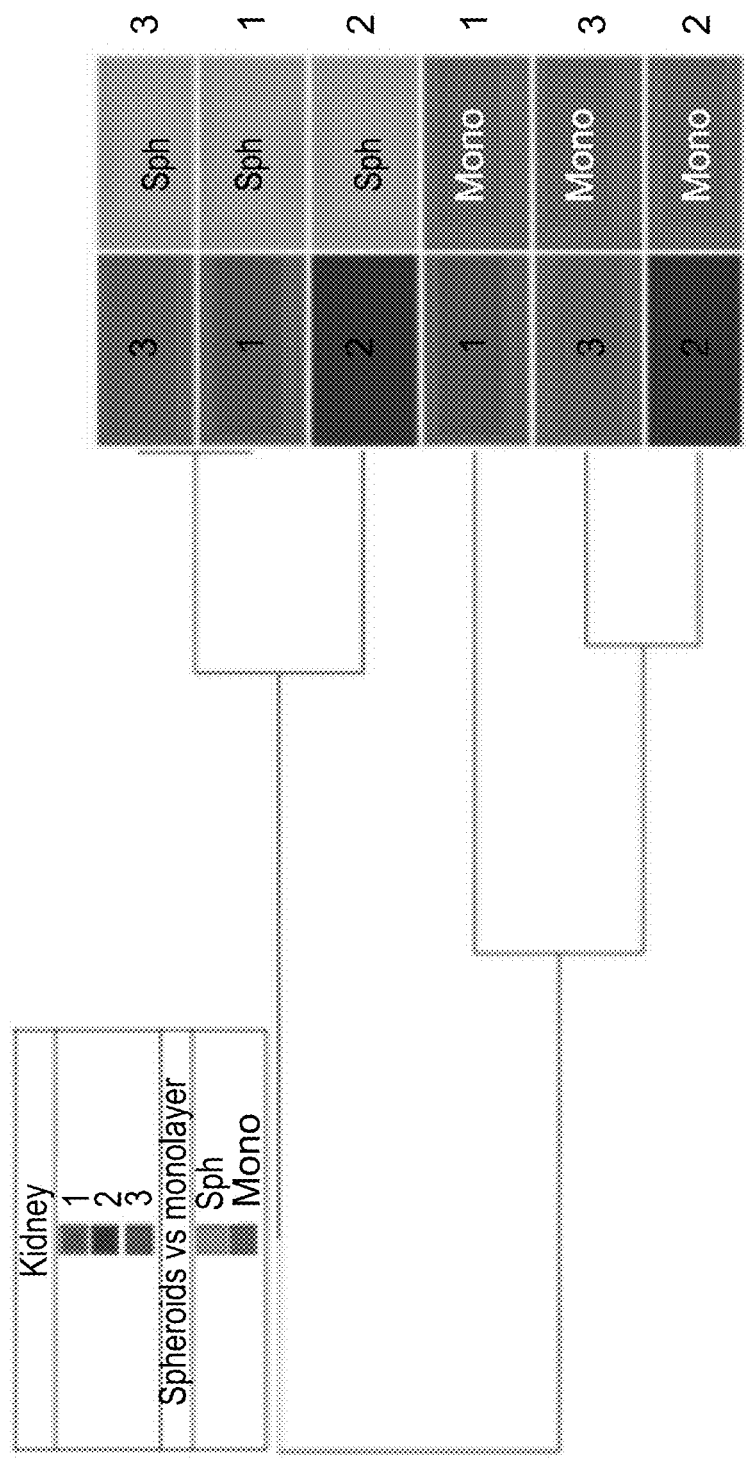
Figure 10B:
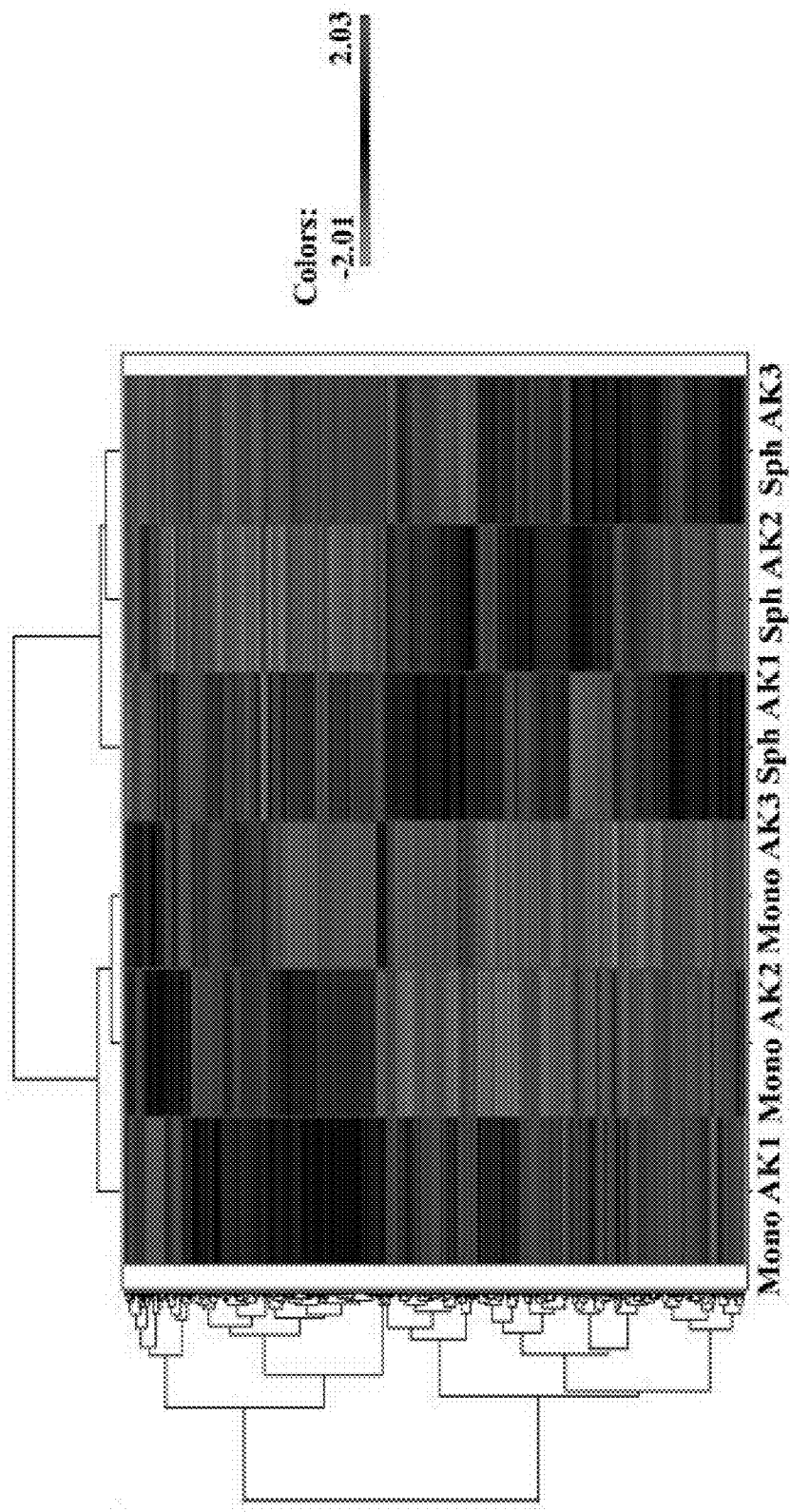
Figure 10C:
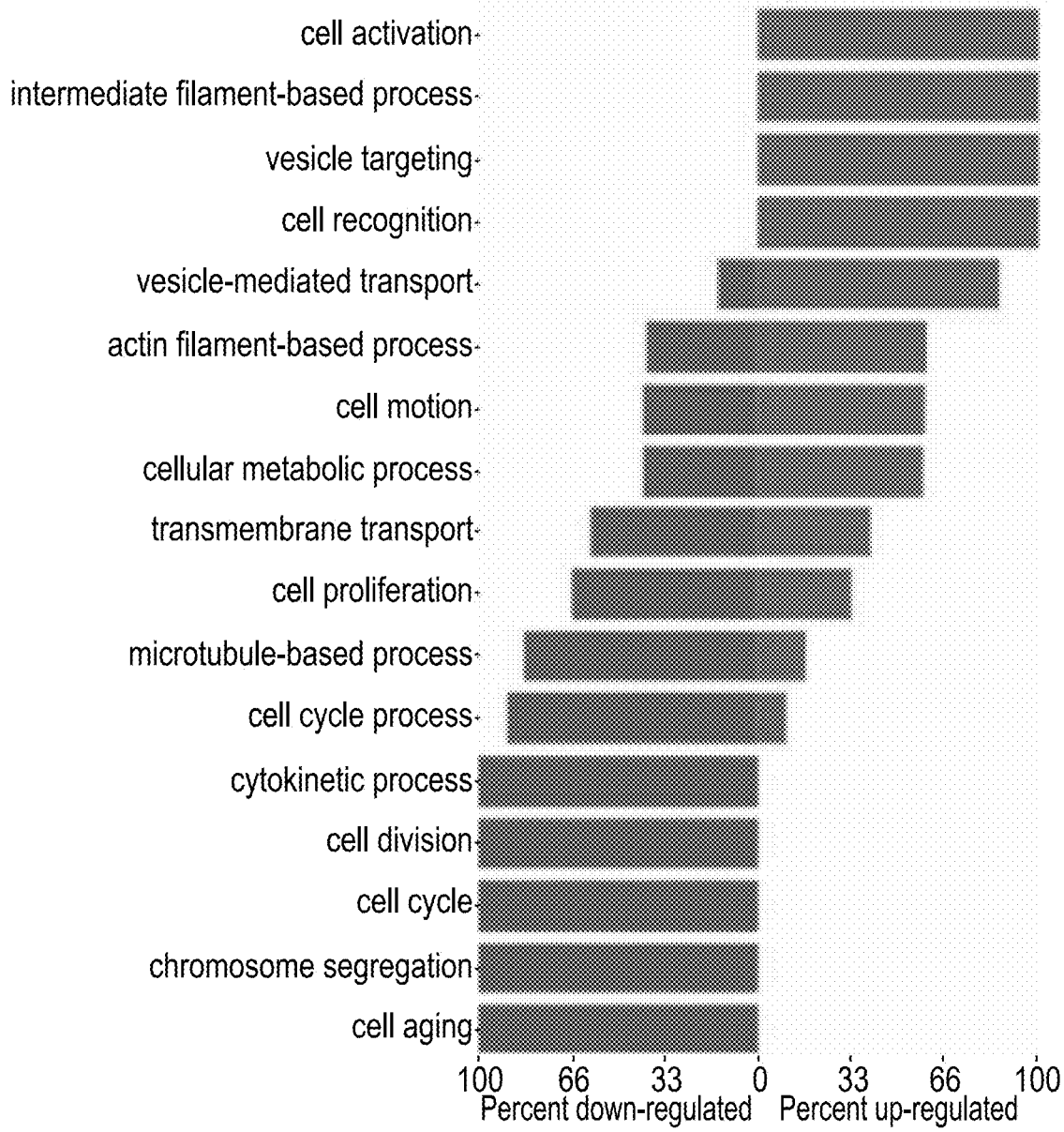

FIGS. 10A-C illustrate the results of microarray analysis of hKEpC spheroids vs. monolayer cells originating from 3 adult kidney (AK) donors. (A) Unsupervised hierarchical clustering separated samples into two different groups: spheroids and monolayer counterparts; (B) Hierarchical clustering of differentially expressed genes. Genes that were either up- (477 genes) or down-regulated (348 genes) in spheroids (Sph AK1-3) at least twofold compared with their monolayer culture counterparts (Mono AK1-3); (C) Forest plot of the cellular processes gene groups representing percent of up- (red) and down (green)—regulated genes.

Figure 11B:
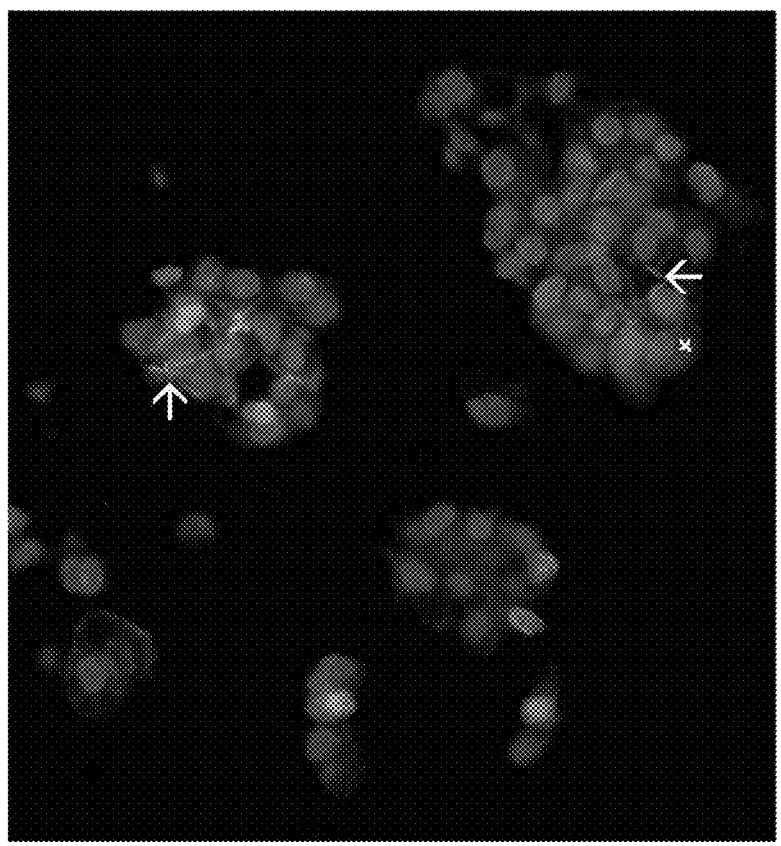
Figure 11A:
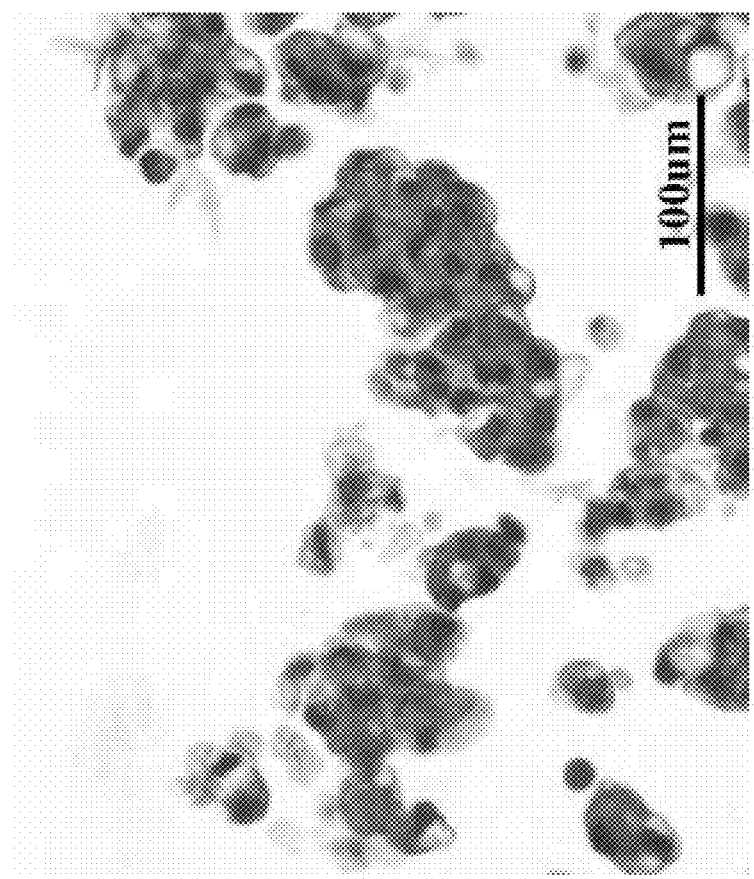
Figure 15A:
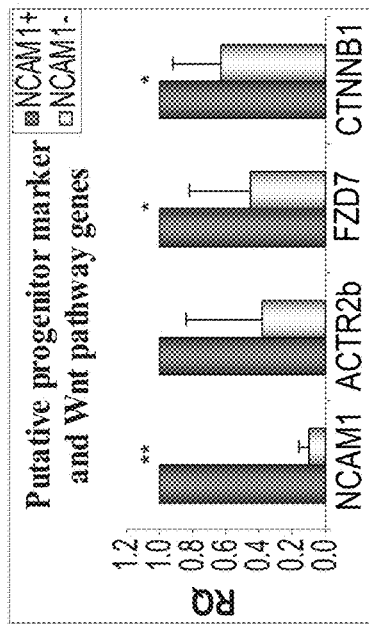
Figure 15B:
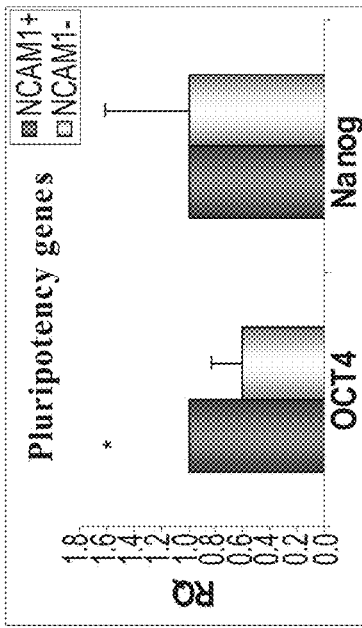
Figure 15C:
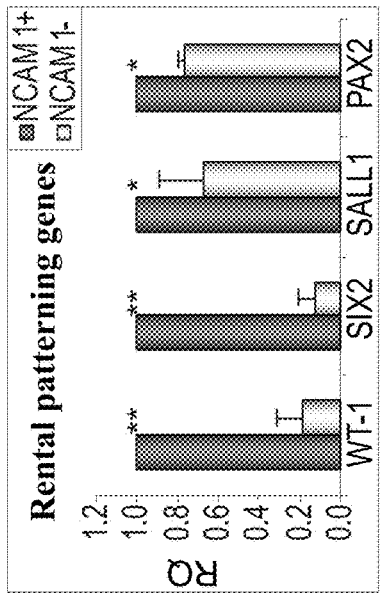
Figure 15D:
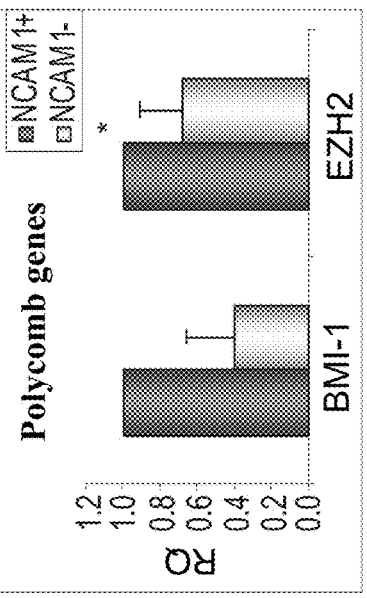
Figure 15E:
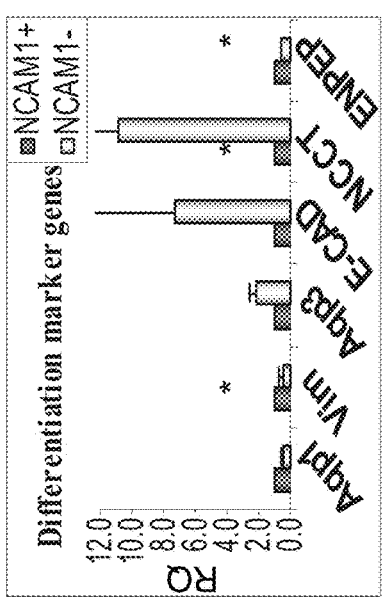

FIGS. 11A-B illustrate hKEpC spheroid characterization and proliferation. FIG. 11A is a photograph illustrating hematoxylin&eosin staining of paraffin embedded spheroids. FIG. 11B is a photograph illustrating immunofluorescence analysis of NCAM and Ki67 of the spheroids. Paraffin embedded spheroids were stained with NCAM (green), Ki67 (red) and Hecht (blue). Low proliferation was observed as evidenced from the low Ki67 staining. Also, low NCAM staining was observed in agreement with FACS analysis.

FIGS. 12A-C are graphs illustrating limiting dilution of primary hAK cultured cells in different media conditions. The graphs represent 3 different experiments on 3 different hAK tissues. hAK seeded in density of 5 and 1 cell per well has higher clonogenic capacity in SCM as opposed to SFM. Highest clonogenic potential was observed with FKCM. (SCM=serum containing media, FKCM=fetal kidney conditioned media (containing serum), SFM=serum free media, SFM from SCM=clones originated in SFM after culture was expanded in SCM).

FIGS. 13A-D are photomicrographs illustrating clone morphology. SCM and FKCM—clones originated from 1 cell/well, SFM—clones originated from 5 cells/well. FKCM clones were more viable and confluent in comparison to SCM.

FIGS. 14A-C are graphs illustrating FACs sorting of NCAM1 expressing hAK cells.

FIGS. 15A-E are bar graphs comparing gene expression between NCAM1+ and NCAM1—cell fractions by quantitative RT-PCR analysis. Cultured hAK cells sorted according to NCAM1 overexpress the renal 'stemness' genes: (a) renal epithelial progenitor genes, wt1, pax2, six2 (Osr1 was also found to be significantly up-regulated, data not shown);

(b) Wnt pathway and renal progenitor surface markers, CTNNB1, FZD7, NCAM1 and ACTR2b; (c) polycomb group, EZH2. In addition, analysis of pluripotency genes (d) showed higher Oct4 levels, while analysis for renal maturation genes (e) showed high vimentin and aminopeptidase A (ENPEP) and low E-cadherin and Na—Cl co-transporter (NCCT), disclosing a proximal tubular origin. The values represent average±SD of at least 3 different experiments on 3 different hAKs. *, $p<0.05$;**, $p<0.005$. Aqp1 and 3 were close to statistical significance.

FIGS. 16A-C are bar graphs illustrating the clonogenic potential of hAK NCAM+ cells. Both positive and negative fraction's cells were plated at 1 and 5 cells per well dilution. NCAM+ cells show high clonogenic potential in all concentrations. Graphs represent three experiments originating from three different hAK tissues.

FIG. 16D is a graph illustrating the results of a MTS proliferation assay performed on hAK cells sorted according to NCAM1. Both positive and negative cell fractions were analyzed 4, 5 and 7 days following sorting. NCAM+ cells showed lower proliferation capacity. Representative graph of three experiments, data represents mean of triplicates. *, $p<0.05$.

FIGS. 16E-J are photomicrographs illustrating the results of a spheroid formation assay performed on $NCAM^+$ and $NCAM^-$ fractions sorted from low-passage cultures and expanded in vitro. $NCAM^+$ cells show ability to form well-defined spheroids, as opposed to $NCAM^-$ cells, which lack that ability, after 7 days in low-attachment conditions.

FIGS. 17A-K are photographs illustrating the results of an in vivo analysis of shperoid and monolayer hKEpC in the chick embryo. $0.43 \times 10^6$ cells, derived from dissociated spheroid and monolayer were grafted on the CAM. FIGS. 9A-B. CAM grafts (arrowheads) generated from (A) spheroids and (B) monolayer cells, 7 days following grafting. Representative photomicrogrpahs of H&E staining of grafts: grafts originated from P2 cultures of spheroids (C), monolayer (D) and from P6 cultures of spheroids (E) and monolayer (F) cells, (G) whole spheroids (P2) (×20) demonstrating extensive tubule formation exclusively by hKEpC spheroids. Grafts originating from (H) mesenchymal stem cells (MSC) and (I) human embryonic kidney cell line (HEK293) used as controls, failed to generate tubules (×10). Control grafts of human fetal kidney (FK) cells originating from $1.25 \times 10^6$ cells (J) did not form any tubules (×10) while $2.5 \times 10^6$ cells (K) generated tubules (marked in arrows) (×20).

FIGS. 18A-D are photomicrographs illustrating that P2 hKEpC spheroids generate segment-specific tubules. Immunoperoxidase (brown) staining of (×20 arrowheads) for segment-specific markers (18A) LTA, (18B) anti-Tamm horsfall glycoprotein (THG) and (18C) DBA. FIG. 18D: Immunofluorescent DBA staining (red) nuclei counterstained with Hoechst (blue). Original magnification ×20.

Figure 19A:
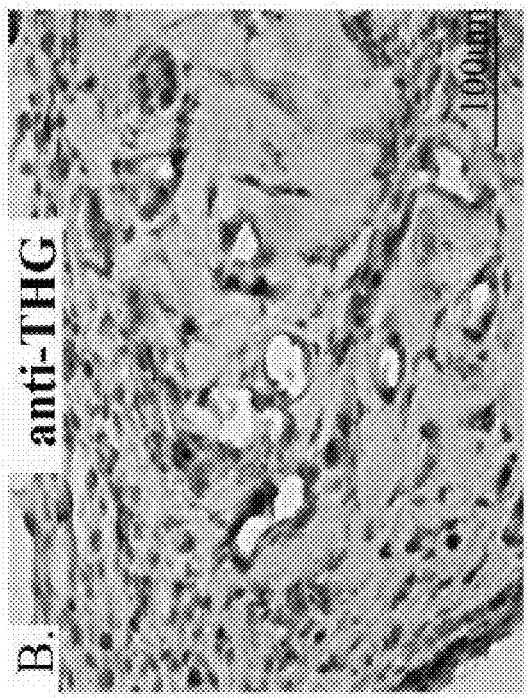
Figure 19B:
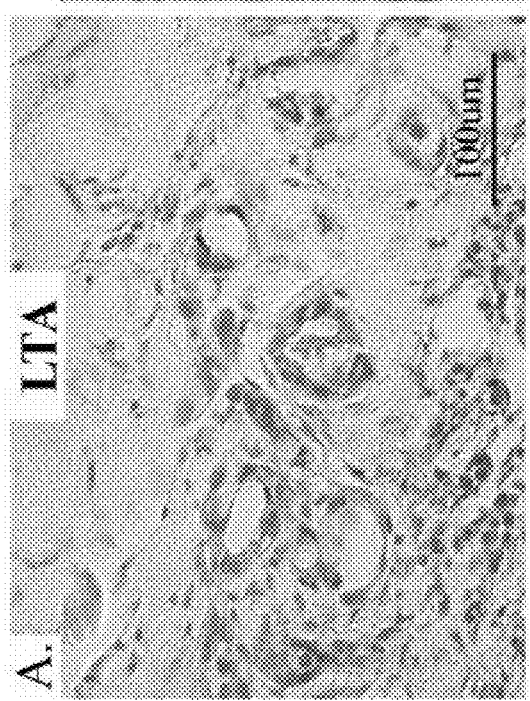
Figure 19C:
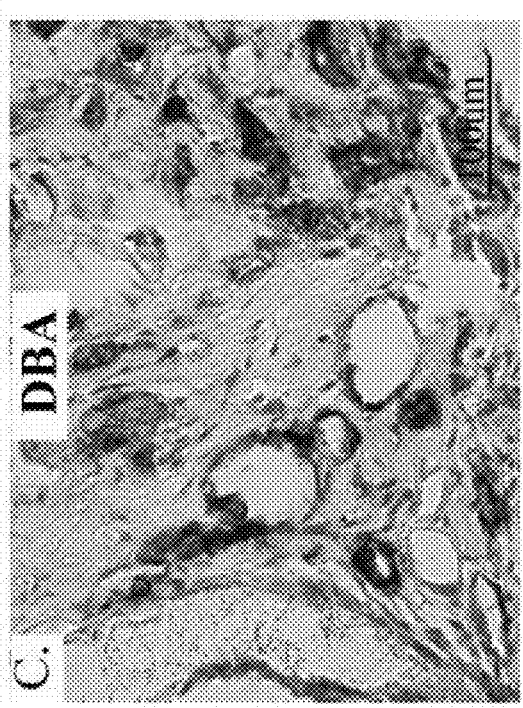
Figure 20A:
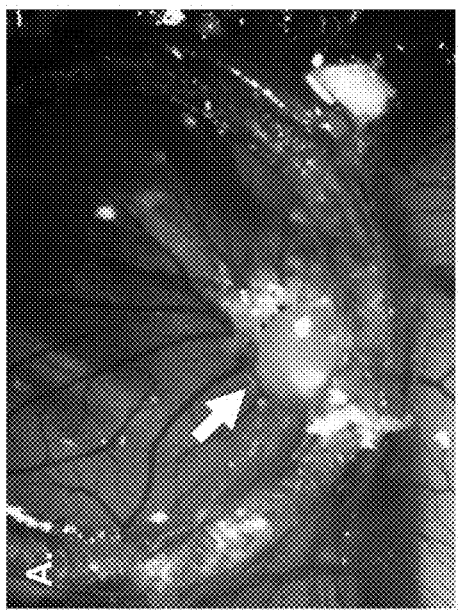
Figure 20B:
Figure 20C:
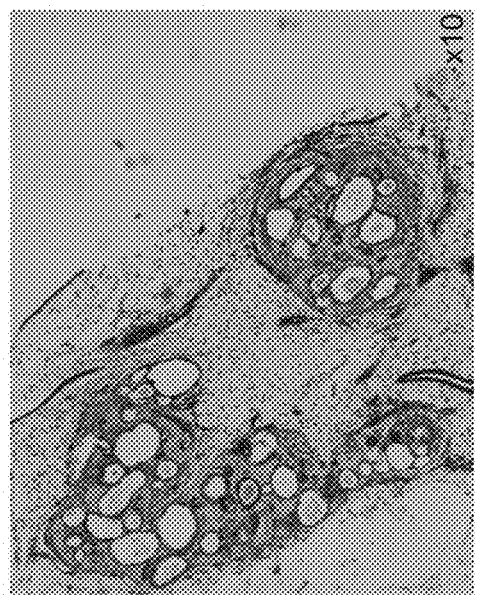
Figures 20D, 20E, 20F:
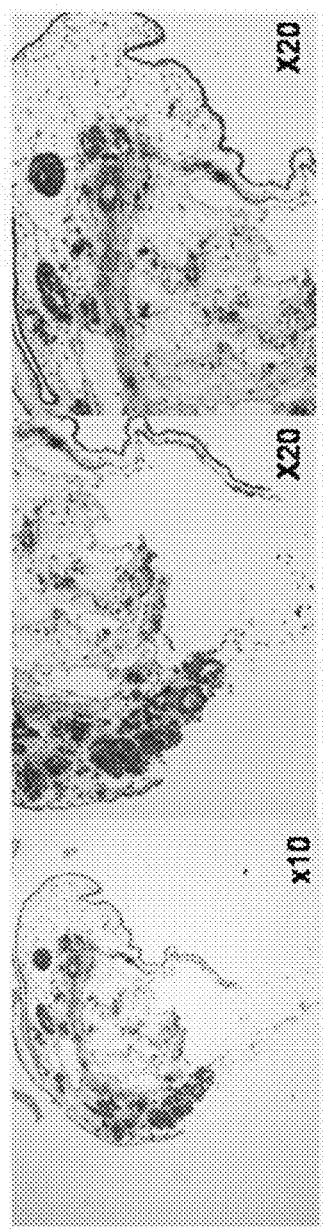

FIGS. 19A-C are photomicrographs of immunoperoxidase (brown) staining of (×20 arrowheads) for segment specific markers (19A) LTA, (19B) THG and (C) DBA. Original magnification ×20.

FIGS. 20A-F are photographs illustrating the results of an in vivo tubulogenesis assay. A. Picture of an explant of hAK cells 7 days after engraftment. Grafting was performed in matrigel B. Flouresence of the explant (cells were labeled with CFSE prior to grating enabling the detection of a flourescent signal). Histological analysis of 7-day grafts (H&E) revealed tubular regeneration by low cell numbers ($0.43 \times 10^6$ cells/egg) only when grafting dissosiated hAK spheroids (C) or hAK NCAM+ cells (D). Tubular structures are highlighted in boxes. Similar cell number of adherent cultured hAK cells did not generate tubular structures (E). Control HEK 293 (F) or mesenchymal stem cells (not shown) did not generate tubular structures and remained as undifferentiated masses.

DESCRIPTION OF SPECIFIC EMBODIMENTS OF THE INVENTION

The present invention, in some embodiments thereof, relates to isolated populations of adult renal cells and methods of isolating and using same.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Renal failure, whether arising from an acute or chronic decline in renal function, is a severe condition that can result in substantial or complete failure of the filtration, reabsorption, endocrine and homeostatic functions of the kidney. It is therefore desirable to obtain progenitor or stem cells capable of developing into renal cells that could substitute for some or all of the functions of the kidney.

Human adult kidney (hAK) stem/progenitor cells are ideal candidates for cell transplantation and tissue engineering. However, their identity remains elusive.

This does not eliminate the possibility of using expanded populations of adult kidney cells as cell-based therapies for tissue engineering and regenerative medicine aimed at improving and restoring renal function. The autologous approach requires isolation of renal cells from a small human tissue sample, expansion in vitro and reintroduction of cells back into the host for renal tissue regeneration. Nevertheless, primary renal epithelia lose their apical-basal polarity, which is characterized by a flattened and elongated morphology and lack of tight junctions, begin to proliferate and dedifferentiate via mechanisms such as epithelial-mesenchymal transition (EMT) after a limited number of passages in monolayer. As the cell number increases, the cells assume the appearance of fibroblasts. Therefore, formation of renal structures may not be adequately achieved by using single kidney cells and appropriate manipulation of renal cells in culture might enhance their functional capacities.

Sphere structures are multicellular globes that develop from cells that survive anchorage-independent conditions in vitro, such as growth in ultra-low attachment plates. Unlike monolayer-based cultures, these structures carry the advantage of mirroring the 3D cellular context. Furthermore, sphere-forming assays have been shown to be a useful means for maintenance and expansion of putative stem/progenitor cell populations.

The present inventor therefore sought to investigate for the first time primary human kidney cells grown in suspension culture over non-adherent plastic surfaces as opposed to monolayer expanded cells. In order to achieve this goal the present inventor isolated primary human renal cells from kidney surgical samples, established heterogeneous cultures of human kidney epithelial cells (hKEpC) and demonstrated their ability to efficiently generate 3D aggregates or spheroids.

It was discovered that the use of serum free medium (SFM) and subsequent low-attachment conditions lead to formation of "nephrospheroids". Epithelial cells present in the nephrospheroids expressed enhanced levels of progenitor and 'stemness' genes including Pax2, Sall1, Six2, Wt1 and as well as the pluripotency gene, Nanog, when compared to adherent culture (FIGS. 8E-H).

In addition, the present inventors have identified a cell surface progenitor marker (NCAM) in cultured human adult kidney which provides for a signature for the isolation of renal stem/progenitor cells. Identification of this marker was very surprising considering it is not expressed in vivo in the adult kidney.

The present inventor showed that NCAM$^+$ enriched adult renal cells overexpressed early renal epithelial progenitor markers (Six2, Osr1, Sall1, Pax2 and Wt1) and early surface antigens (FZD7, AVR2b) (11), polycomb group (Bmi-1, Ezh2), Wnt pathway (Beta-catenin, FZD7) as well the pluripotency marker, Oct4 (FIGS. 9A-E), indicating the presence of stem/progenitor cells. The NCAM$^+$ subpopulation was highly clonogenic (FIGS. 16A-C) and further comprised sphere generating capabilities (FIGS. 16E-J) further indicating the presence of stem/progenitor cells.

Whilst further reducing the present invention to practice, the present inventor showed that both spheroid-forming and NCAM+ cells efficiently regenerated tubular structures when grafted in the chick embryo (FIGS. 17A-C).

These results provide a feasible approach for experimental cell sorting of adult human renal progenitors as well as a framework for developing cell selection strategies for renal cell-based therapies.

Thus, according to one aspect of the present invention there is provided an isolated cell population of human adult kidney cells, comprising at least 50%, 60%, 70% 80% or 90% adult renal stem having a NCAM+ signature.

As used herein, the term "isolated" means that a cell population is removed from its natural environment. As used herein, the term "purified," means that a cell population is essentially free from any other cell type (e.g., feeder fibroblasts).

As used herein the phrase "renal stem cell" refers to a cell which is not terminally differentiated as a renal cell but which has the ability to differentiate into specialized cell having one or more structural and/or functional aspects of a physiologic kidney. According to specific embodiments the renal stem cells are not embryonic stem cells.

According to an exemplary embodiment, at least 50%, 60%, 70% 80% or 90% of the renal stem cells have a NCAM+CD133+ signature.

According to another embodiment, at least 50%, 60%, 70% 80% or 90% of the renal stem cells have a NCAM+ CD133− signature.

According to another embodiment, at least 50%, 60%, 70% 80% or 90% of the renal stem cells have a NCAM+ CD24+ signature.

According to another embodiment, at least 50%, 60%, 70% 80% or 90% of the renal stem cells have a NCAM+ CD24− signature.

According to another embodiment, at least 50%, 60%, 70% 80% or 90% of the renal stem cells have a NCAM+ nestin+ signature.

According to another embodiment, at least 50%, 60%, 70% 80% or 90% of the renal stem cells have a NCAM+ nestin− signature.

NCAM+ populations of the present invention further comprise a gene expression profile as provided in FIGS. 15A-E. Assaying expression of any of the genes of the provided expression profile may be used to qualify cells of the NCAM+, signature as further described herein below.

The present invention further provides for a method of isolating the aforementioned cells. This is effected by enriching for a subpopulation of renal cells from a human adult renal tissue, the subpopulation of renal cells having an NCAM+ signature.

Thus a human adult kidney is provided. The kidney may comprise a whole kidney or fragments thereof (e.g., renal capsule). Typically the cells of the adult kidney are of a heterogeneous population.

The cells of the adult kidney may be dispersed prior to selection. Exemplary agents that may be used to disperse the kidney cells include collagenase, dispase and trypsin.

According to one embodiment, the cells of the adult kidney are expanded prior to sorting. Typically the cells are cultured for less than three passages, more preferably for less than two passages.

Below is a list of some of the exemplary markers of the present invention with their accession numbers.

NCAM1 (3 variants): NM_181351, NM_000615, NM_001076682; FZD7: NM_003507; CD24: NM_013230; CD133 (PROM1): NM_006017; NTRK2: AF410902; PSA-NCAM, Polysialylated NCAM1 same ID as NCAM1; ACVRIIB: NM_001106; ROR2 (2 variants): M97639 NM, 004560; oct4 (POU5F1): NM_203289 NM_002701; six2: NM_016932 (accession number: AF136939); sall1: NM_002968; ctnnb1 NM_001098210 (NM_001098209 XM_001133660 XM_001133664 XM_001133673 XM_001133675 NP_001091679 XP_001133660 XP_001133664 XP_001133673 XP_001133675); vimentin: NM_003380 (accession number: M14144); Bmi1: NM_005180 (accession number BC011652); ezh2 (2 variants): NM_152998 NM_004456; nanog: NM_024865 (accession number: AB093576 (complete); aqp1—NM_000385 (accession number: M77829); aqp3: NM_004925; e-cadherin (CDH1): NM_004360 (accession number: L08599); nestin (NES) NM_006617.1.

Antibodies for the above mentioned cell markers are commercially available. Examples include but are not limited to, NCAM1 (eBioscience), EPCAM (MiltenyiBiotec), FZD7 (R&D Systems), CD24 (eBioscience), CD133 (MiltenyiBiotec), NTRK2 (R&D Systems), PSA-NCAM (MiltenyiBiotec) ACVRIIB (R&D Systems), ROR2 (R&D Systems), nestin (Abcam).

As used herein, the term "enriching" refers to a procedure which allows the specific subpopulation of renal cells to comprise at least about 50%, preferably at least about 70%, more preferably at least about 80%, about 95%, about 97%, about 99% or more renal stem cells having the desired signature (e.g. NCAM+).

The enriching may be effected using known cell sorting procedures such as by using a fluorescence-activated cell sorter (FACS).

As used herein, the term "flow cytometry" refers to an assay in which the proportion of a material (e.g. renal cells comprising a particular maker) in a sample is determined by labeling the material (e.g., by binding a labeled antibody to the material), causing a fluid stream containing the material to pass through a beam of light, separating the light emitted from the sample into constituent wavelengths by a series of filters and mirrors, and detecting the light.

A multitude of flow cytometers are commercially available including for e.g. Becton Dickinson FACScan and FACScalibur (BD Biosciences, Mountain View, Calif.). Antibodies that may be used for FACS analysis are taught in Schlossman S, Boumell L, et al, [Leucocyte Typing V. New York: Oxford University Press; 1995] and are widely commercially available.

Another method of cell sorting is magnetic cell sorting as further described in the Examples section below.

It will be appreciated that the enriching may also be effected by depleting of non-relevant subpopulations such as renal stromal cells or interstitium (interstitial) cells.

Once isolated, cells of the present invention may be cultured and their "stemness" properties may be further analyzed as described below.

Since clonogenicity is a function of stem cells, the cells may be analyzed for their clonogenic potential. The present inventors have shown that isolated adult renal cells having an NCAM+ signature are highly clonogenic.

An exemplary method for ascertaining clonogenic potential is described in the Example section below.

The present inventor has discovered that culturing cells at low dilution in serum-comprising medium, preferably in the presence of conditioned medium from human fetal kidney cells is an optimal way to ascertain clonogenic potential. By counting the number of clones formed after a predetermined time (e.g. one month), one can determine the clonogenic potential of a renal cell population.

(b) counting a number of clones formed from the adult renal cells of the population, thereby determining clonogenic potential of an adult renal cell population.

An exemplary method for obtaining conditioned medium from human fetal kidney cells is by combining (e.g. in q 1:1 ratio) SCM and SCM from FK cultures of passages 1 to 3.

The ability to form spheres is also a function of stem cells. Accordingly, the cells may be analyzed for their sphere-forming potential. The present inventors have shown that isolated adult renal cells having an NCAM+ signature have a high sphere forming potential.

An exemplary method for ascertaining sphere-forming potential is described in the Example section below.

Another way to confirm the presence of renal stem cells is by testing for expression of stem cell-specific genes. An upregulation of such genes infers the presence of renal stem cells. Such genes include, but are not limited to Six2 (NM_016932-accession number: AF136939), osr1 (NM_145260.2), Pax2 (NM_003987.3 NM_000278.3, NM_003988.3, NM_003989.3, NM_003990.3), Sall1 (NM_002968) and Cited 1 (NM_001144885.1, NM_001144886.1, NM_001144887.1 NM_004143.3). Methods for analyzing for the expression of stem cell-specific genes include RT-PCR, Northern blot, Western blot, flow cytometry and the like.

As mentioned, the present inventor has found optimal conditions for culturing adult kidney cells such that they form spheroids. The present inventor found that these spheroids expressed stem cell-specific genes to a greater extent than adult kidney cells that were cultured under adherent conditions.

Thus, according to another aspect of the present invention there is provided a method of generating a nephrospheroid, the method comprising culturing adult kidney cells under non-adherent conditions, thereby generating the nephrospheroid.

As used herein, the term "nephrospheroid" refers to a 3 dimensional (spherical or partially) aggregate of kidney cells. It may also be referred to as a tubular organoid. The nephrospheroid comprises at least two cell types and is not derived from a single cell-type (i.e. is not of a clonal origin).

According to one embodiment the nephrospheroid is capable of generating proximal distal tubules and collecting ducts when allowed to differentiate in vivo following grafting to the chorioallantoic membrane (CAM) of the chick embryo.

According to another embodiment, the nephrospheroid is not capable of generating proximal distal tubules and collecting ducts when allowed to differentiate in vivo following grafting to the chorioallantoic membrane (CAM) of the chick embryo.

The phrase "non-adherent conditions" refers to conditions in which the cells do not attach to the surface of a container in which they are cultured such that a substantial portion of the cells can be removed from the surface of the container by mechanical manipulations that do not cause significant damage to the cells. It is understood that the cells can still be retained in or on a non-adherent matrix (e.g., on Hydrogel spheres) and be removed from the surface of the container. Such manipulations include, for example, gentle agitation, massage, or manual manipulation of the container, or rinsing the container with growth media As used herein, a substantial portion of the cells to be removed is at least 70%, preferably at least 75%, 80% or 85%, more preferably at least 90% or 95%. Manipulations that cause damage to the cells can be identified by determining the viability of the cells before and after manipulation, for example by trypan blue staining. Mechanical manipulations should cause damage to less than 20%, preferably less than 15%, or 10%, more preferably less than 5%, 2%, or 1% of the cells. Numerous methods are known for culturing cells under non-adherent conditions. These include growth of cells encapsulated in matrices such as Hydrogel and Matrigel™, on in between layers of agarose, or in Teflon™ bags. An exemplary hydrogel which may be used is PolyHEMA. It will be appreciated that the cells can grow in contact with the non-adherent matrices, but do not adhere to plastic culture containers.

Contemplated culture mediums include, but are not limited to IMDM (Invitrogen) or DMEM (Invitrogen).

According to one embodiment, the culture medium comprises serum.

According to another embodiment, the culture medium is devoid of serum.

The medium may comprise additional components which further encourage the cells to form spheroids. Thus, for example, the medium may further comprise growth factors such as epidermal growth factor (EGF) and fibroblast growth factor (FGF). Other contemplated components include insulin and progesterone.

Typically, prior to culturing the adult kidney cells, the cells are dispersed as described herein above.

Optionally, the adult kidney cells are cultured prior to forming the spheroids in order to expand the number of cells.

According to one embodiment, the adult kidney cells are expanded in serum containing medium for about 4, 5, 6, 7 or more passages under adherent conditions prior to generation of the spheroids.

The phrase "adherent conditions" refers to conditions in which the cells attach to the surface of a container in which they are cultured such that a substantial portion of the cells cannot be removed from the surface of the container by mechanical manipulations that do not cause significant damage to the cells.

Using the above described method, the present inventor generated nephrospheroids and proceeded to characterize these structures.

According to one embodiment, an isolated nephrospheroid may be characterized by enhanced expression of at least one polypeptide selected from the group consisting of sall1, pax2, six2 and WT1 or combinations thereof, as compared to identical adult kidney cells grown under adherent conditions.

According to one embodiment, an isolated nephrospheroid may be characterized by enhanced expression of each of sal1, pax2, six2 and WT1 as compared to identical adult kidney cells grown under adherent conditions.

As used herein, the term enhanced expression refers to an increase in expression by at least 1.5 fold, more preferably at least 2 fold and even more preferably at least 3 fold.

Once generated the cell populations of the present invention (including the NCAM+ populations and the nephrsopheres) are typically allowed to proliferate under conditions that preserve their stem/progenitor cell phenotype.

Cell populations of the present invention can be genetically modified to express a transgene. This may be used to increase survival of the cells, render them immortalized or differentiated to a desired lineage. Examples of such transgenes and methods of introducing the same are provided below.

Candidate genes for gene therapy include, for example, genes encoding the alpha 5 chain of type IV collagen (COL4A5), polycystin, alpha-galactosidase A, thiazide-sensitive sodium chloride cotransporter (NCCT), nephrin, actinin, or aquaporin 2.

Further, genes encoding erythropoeitin or insulin can be introduced into a kidney stem cell. For treatment of anemia associated with renal failure or diabetes it can be useful to introduce into a patient a stem cells modified to express erythropoeitin or insulin. The renal stem cells can be stably or transiently transfected with DNA encoding any therapeutically useful polypeptide.

The cell populations of the invention can also be provided with a transgene encoding VEGF or some other factor that can promote growth and or differentiation of cells.

These genes can be driven by an inducible promoter so that levels of the transgen can be regulated. These inducible promoter systems may include a mutated ligand binding domain of the human estrogen receptor (ER) attached to the protein to be produced. This would require that the individual ingest tamoxifen to allow expression of the protein. Alternatives are tetracyclin on or off systems, RU486, and a rapamycin inducible system. An additional method to obtain relatively selective expression is to use tissue specific promoters. For instance, one could introduce a transgene driven by the KSP-cadherin, nephrin or uromodulin-specific promoter.

Cells isolated or generated by the method described herein can be genetically modified by introducing DNA or RNA into the cell by a variety of methods known to those of skill in the art. These methods are generally grouped into four major categories: (1) viral transfer, including the use of DNA or RNA viral vectors, such as retroviruses (including lentiviruses), Simian virus 40 (SV40), adenovirus, Sindbis virus, and bovine papillomavirus for example; (2) chemical transfer, including calcium phosphate transfection and DEAE dextran transfection methods; (3) membrane fusion transfer, using DNA-loaded membrane vesicles such as liposomes, red blood cell ghosts, and protoplasts, for example; and (4) physical transfer techniques, such as microinjection, electroporation, or direct "naked" DNA transfer. Cells can be genetically altered by insertion of pre-selected isolated DNA, by substitution of a segment of the cellular genome with pre-selected isolated DNA, or by deletion of or inactivation of at least a portion of the cellular genome of the cell. Deletion or inactivation of at least a portion of the cellular genome can be accomplished by a variety of means, including but not limited to genetic recombination, by antisense technology (which can include the use of peptide nucleic acids, or PNAs), or by ribozyme technology, for example. Insertion of one or more pre-selected DNA sequences can be accomplished by homologous recombination or by viral integration into the host cell genome. The desired gene sequence can also be incorporated into the cell, particularly into its nucleus, using a plasmid expression vector and a nuclear localization sequence. Methods for directing polynucleotides to the nucleus have been described in the art. The genetic material can be introduced using promoters that will allow for the gene of interest to be positively or negatively induced using certain chemicals/drugs, to be eliminated following administration of a given drug/chemical, or can be tagged to allow induction by chemicals (including but not limited to the tamoxifen responsive mutated estrogen receptor) for expression in specific cell compartments (including but not limited to the cell membrane).

Calcium phosphate transfection, which relies on precipitates of plasmid DNA/calcium ions, can be used to introduce plasmid DNA containing a target gene or polynucleotide into isolated or cultured cells. Briefly, plasmid DNA is mixed into a solution of calcium chloride, then added to a solution which has been phosphate-buffered. Once a precipitate has formed, the solution is added directly to cultured cells. Treatment with DMSO or glycerol can be used to improve transfection efficiency, and levels of stable transfectants can be improved using bis-hydroxyethylamino ethanesulfonate (BES). Calcium phosphate transfection systems are commercially available (e. g., ProFection from Promega Corp., Madison, Wis.).

DEAE-dextran transfection, which is also known to those of skill in the art, may be preferred over calcium phosphate transfection where transient transfection is desired, as it is often more efficient.

For isolated cell populations, microinjection can be particularly effective for transferring genetic material into the cells.

The developmental potential of the cell populations thus obtained can be investigated using methods which are well known in the art. For example by injection into other organs (liver, muscle, heart and bone marrow) to test their multipotency Clarke et al. describes protocols for investigating the development potential of stem cells (Clarke et al. 2000 Science 288:1660). The cell popualtions may also be grated into chick embryos so as to ascertain their developmental potential as described in the Examples section herein below.

The cell populations of the invention (or cells which have been differentiated therefrom) can be used to supplement or substitute for kidney cells that have been destroyed or have reduced function. Thus, they can be used to treat patients having poor or no kidney function. The cell populations of the invention or cells derived there from may be capable of performing the filtration and reabsorptive/secretive functions of the kidney.

Thus according to an aspect of the present invention there is provided a method of treating a renal damage in a subject in need thereof comprising administering to the damaged kidney of the subject a therapeutically effective amount of the isolated population of cells described herein, thereby treating the renal disease in the subject.

Cells of the present invention can be used to treat any form of acute or chronic kidney disease, diabetic nephropathy, renal disease associated with hypertension, hypertensive acute tubular injury (ischemic, toxic), interstitial nephritis, congenital anomalies (Aplasia/dysplasia/obstructive uropathy/reflux nephropathy); hereditary conditions (Juvenile nephronophtisis, ARPCKD, Alport, Cystinosis, Primary Hyperoxaluria); Glomerulonephritides (Focal Segmental Glomerulosclerosis); Multisystem Diseases (SLE, HSP, HUS).

The present inventor contemplates administration of single cell suspensions of dissociated spheroid-cells, partly dissociated spheroid-cells or non-dissociated spheroid cells.

The cells may be administered per se or as part of a pharmaceutical composition where they are mixed with a suitable carrier or excipient.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the renal progenitor cells (or cells differentiated therefrom) accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

The cell populations or cells derived (e.g. differentiated therefrom) can be administered into a subject such as surgically or by infusion. For example, renal cells are injected in vivo into a kidney that is in the postischemic recovery phase. This can be tested easily in an animal model predictive of ischemic kidney damage, the renal pedicle of an anesthetized mouse is clamped for 30 minutes to induce kidney ischemia. Renal stem cells are then injected into the juxtamedullary region (approximately 2000 cells at a depth of 2-4 mm). After 2 weeks of recovery, immunohistochemical analysis is used as described above to look for differentiated cells surface markers GP330, Tamm-Horfall, *Dolichos biflorous*, and the like. Post-incorporation differentiation status can then be compared to pre-injection marker status.

The cells of the invention, or cells derived there from (e.g., epithelial cells endothelial cells, mesangial cells, vascular smooth muscle cells, and pericytes) can be used to construct artificial kidney systems. Such a system can be based on a hollow fiber filtration system.

In one example of a filtration device, the stem cells of the invention or differentiated progeny thereof are grown on the interior of hollow fibers having relatively high hydraulic conductivity (i.e., ultrafiltration coefficient). The hollow fiber passes through a chamber that is provided with a filtrate outlet port. Arterial blood containing metabolic waste and other unwanted material is introduced into one end of the hollow fiber through an inlet port. Blood passed through the fiber and exits the other end of the fiber through an outlet port where it passed into the patient's vascular venous flow. As blood passes through the fiber, filtrate pass through the cells lining the interior of the fiber and through the hollow fiber itself. This filtrate then passes out of the chamber containing the fiber through the filtrate outlet port. The device preferably includes many such hollow fibers each of which can be in its own chamber. Alternatively many, many hollow fibers (100-100,000 or even more) can be bundled together in a single chamber.

The cells of the invention can be used to create a tubule-processing device. In such a device the stem cells of the invention or differentiated cells derived from the stem cells of the invention can be grown in a layer on the exterior of the semipermeable hollow fiber (i.e. a scaffold). The fiber is placed in a chamber that is provided with an inlet port and an outlet port. As ultrafiltrate from filtered blood flows through the chamber, reabsorbant passes through the cell layer and through the wall of the fiber into the lumen of the fiber from which it can be directed back into the patient's systemic circulation. Ultrafiltrate that is not reabsorbed passes through the outlet port of the chamber.

In the devices described above, it can be desirable to coat the fiber surface that will bear the cell layer with extracellular matrix components. For example, the fiber can be coated with materials such as collagen (e.g., Type I collagen or Type IV collagen), proteoglycan, fibronectin, and laminin or combinations thereof. It can be desirable to combine various cell types on the inner or outer surface of the fibers. For example, it can be desirable to include endothelial cells and pericyte, vascular smooth muscle cells or mesangial cells or fibroblasts or combinations thereof. It can also be useful to provide a feeder layer of cells, e.g., irradiated fibroblasts or other cells that can provide soluble factors and structural support to cells they are indirectly or directly in contact with.

The above-described filtration system and the above-described tubule processing system can be combined to create an artificial kidney. Such systems are described in U.S. Pat. No. 6,150,164, hereby incorporated by reference. A number of suitable materials for forming the hollow fiber are described in U.S. Pat. No. 6,150,164, hereby incorporated by reference.

The present invention provides a method of using the cell populations of the present invention to characterize cellular responses to biologic or pharmacologic agents involving isolating the cells as described s, culture expanding the cells to establish a plurality of MRPC cultures, contacting the MRPC cultures with one or more biologic or pharmacologic agents, identifying one or more cellular responses to the one or more biologic or pharmacologic agents, and comparing the one or more cellular responses of the cultures. Tissue culture techniques known to those of skill in the art allow mass culture of hundreds of thousands of cell samples from different individuals, providing an opportunity to perform rapid screening of compounds suspected to be, for example, teratogenic or mutagenic.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Methods

Cell Cultures of Human Adult Kidney (hAK):

Normal hAK samples were retrieved from borders of RCC tumors from partial and total nephrectomy patients. This procedure was done following informed consent and has been approved by the local ethical committee. The samples were minced in HBSS, soaked in collagenase for 2 hours and then cultured in serum containing medium, (SCM) or in serum free medium (SFM). SCM comprised IMDM medium supplemented with FBS 10%, L-Glutamin 1%, Pen-Strep 1% and growth factors: 50 ng/ml of bFGF, 50 ng/ml of EGF and 5 ng/ml of SCF (R&D systems). SFM comprised 500 ml DMEM:F12 (ratio 1:1, Invitrogen), 1% Pen-strep, 2 ml B27 supplement (Gibco), 4 µg/ml heparin, 1% Non essential Amino acids (invitrogen), 1% of sodium pyruvate (invitrogen), 1% L-glutamine, 1 ml Lipid mix (Sigma), 5 ml N2 supplement 100× (Gibco), 5 ml growth factor mix (for 200 ml of growth factor mix: 100 ml DMEM:F12, 4 ml 30% glucose, 200 mg transferin, 50 mg insulin in 20 ml of water, 19.33 mg putrescine in 20 ml ddw, 200 µl sodium selenite (0.3 mM stock), 20 µl progesterone (2 mM stock)), FGF 10 ng/ml, EGF 20 ng/ml. Upon 90% confluence, cells were split. Medium was changed every 3 days. Spheroid formation was tested by seeding the cells in PolyHEMA pre-coated plates, in the SFM. Fetal kidney conditioned medium (FKCM) was obtained by combining in the 1:1 ratio SCM and SCM from FK cultures of passages 1 to 3.

Antibodies for FACS Analysis:

Primary fluorochrome conjugated anti-human antibodies against: CD133/1:APC, CD133/1:PE, CD34:FITC, PSA-NCAM:PE (Miltenyi Biotech), NCAM:APC (Biolegend), NCAM:PE (eBioscience), CD90:FITC (Biosciences Pharmingen, BD), CD105:FITC (Serotec), CD24:PE (eBioscience), C-Kit:APC (eBioscience), CD45:FITC (R&D systems). Primary unconjugated anti human antibodies against: ACVR2B, FZD7, NTRK2 (R&D systems). In order to visualize the primary unconjugated antibodies, appropriate secondary antibodies were used conjugated to either Alexafluor-488 or Alexafluor-647 (Molecular Probes, INC.). 7-amino-actinomycin-D (7-AAD, BD Biosciences) was used for dead cells exclusion from the analysis.

FACS Analysis:

Monolayer cells were detached from culture plates with 0.25% trypsin (Gibco), spheroids were collected and dissociated by 5-10 min digestion with Accutase (Sigma-Aldrich). Viable cell number was determined using Trypan blue staining (Invitrogen). Cells ($1\times10^5$ in each reaction) were suspended in 50 µl of FACS buffer [0.5% BSA and 0.02% sodium acid in PBS (Sigma-Aldrich and Invitrogen, respectively)] and blocked with FcR Blocking Reagent (MiltenyiBiotec, Auburn, USA) and human serum (1:1) for 15 min at 4° C. Cells were then incubated for 45 min with a respective antibody or a matching isotype control. Cell viability was tested using 7AAD viability staining solution (eBioscience). Cell labeling was detected using FACSCalibur (BD Pharmingen). Flow cytometry results were analyzed using FlowJo analysis software. Viable cells were defined by their FSC/SSC profiles and, in addition, their lack of 7AAD. Detection of cells with high ALDH1 enzymatic activity was performed using the ALDEFLUOR kit (StemCell Technologies, Durham, N.C., USA) according to the kit's protocol.

Magnetic Cell Sorting:

CD56 (NCAM) microbeads (Miltenyi Biotec) were used for single marker cell separation. Positive and negative fractions were separated using Mini or MidiMACS cell columns (Miltenyi Biotech) according to the manufacturer's protocols. Briefly, cell suspension was obtained and, for the removal of clumps, was passed through a 30 µm nylon mesh. Cells were labeled by adding 20 µl CD56 microbeads per $10^7$ total cells for 15 minutes in refrigerator. Then the cells were washed, resuspended and magnetically separated. For increased purity, the fractions passed a second time through fresh columns. Separated cells were plated for limiting dilution, differentiation assays and FACS analysis. A part of cells was used for RNA extraction.

On the next day, purity of sorted fractions was checked by FACS analysis, after fluorescent labeling.

FACS Sorting:

Cells were harvested as described above, filtered through a 30 µm nylon mesh before final centrifugation, then resuspended in flow cytometry buffer consisting of 2 mM bovine serum albumin (BSA; Sigma-Aldrich) and 10% sodium azide in PBS. Cells were labeled with anti NCAM:PE (eBioscience) or other needed antibody. Fluorescence-activated cell sorter FACSAria and the FACSDiva software (BD Biosciences) were used in order to enrich for cells expressing these markers. Single viable cells were gated on the basis of 7-amino-actinomycin-D (7-AAD, BD Biosciences) stained cell exclusion, and then physically sorted into collection tubes for limiting dilution plating and RNA extraction. Data were additionally analyzed and presented using FlowJo software (Tree Star). Purity of sorted fractions was checked visually and by FACS reanalysis.

Gene Expression Analysis of the Separated Cell Fractions:

Quantitative real time reverse transcription PCR (qPCR) reactions were carried out to determine fold changes in expression of the selected renal 'stemness' genes (57) as well of differentiation markers in the sorted hAK cells.

The following nephron segment-specific genes were analyzed: Aminopeptidase-A (ENPEP), Aquaporin-1 (AQP1), Aquaporin-3 (AQP3), Na/CL co-transporter (NCCT), Podocin; renal stem/progenitor genes: PAX2, SALL1, SIX2, WT1 and pluripotency gene: NANOG.

Primers were obtained from Applied Biosystems. RNA was extracted using the micro or miniRNeasy kits (Qiagen) according to the manufacturer's protocols. cDNA synthesis was carried out using the High Capacity cDNA RT kit (Applied Biosystems). Each analysis reaction was performed in triplicate. GapDH or HPRT1 were used as endogenous controls throughout all experimental analyses. Gene expression analysis was performed using TaqMan Gene Expression Assays (Applied Biosystems). Analysis was performed using the $-\Delta\Delta Ct$ method, which determines fold changes in gene expression relative to a comparator sample (the positive fraction of each hAK).

Clonogenicity of hAK Stem/Progenitor Cells:

Limiting dilution assay was performed on separated cell fractions NCAM1 positive vs. NCAM1 negative. Briefly, sorted cells were plated in 96-well micro well plates (Greiner Bio-One) in 150 µl of culture media, at 0.3 or 1 cells per well dilution. The low cell concentration was achieved by serial dilutions reaching 1000 cells per ml. The number of colonized wells was recorded after one month.

Immunohistochemical Staining of hAK:

Sections, 4-µm thick, from whole blocks of normal hAK were cut for immunohistochemistry. The sections were processed within 1 week to avoid oxidation of antigens. Before immunostaining, sections were treated with 10 mM citrate buffer, PH 6.0 for 10 min at 97° C. in a microwave oven for antigen retrieval, followed by treatment of 3% $H_2O_2$ for 10 minutes. The slides were subsequently stained by the labeled—(strept) avidin-biotin (LAB-SA) method using a histostain plus kit (Zymed). Anti-human CD56 antibody (LifeSpan Biosciences, Inc.) and anti-FZD7 antibody, at a dilution of 1:50, were used. Controls were prepared by omitting the primary antibodies or by substituting the primary antibodies with goat IgG isotype. The immunoreaction was visualized by an HRP-based chromogen/substrate system, (Zymed).

Immunofluorescent Staining of Nephrospheroids:

Spheroids were collected, fixed in PFA 4%, embedded in agarose gel and then in paraffin. Immunocytochemistry for Ki67 (mammalian-specific monoclonal rabbit antibody, Lab Vision clone SP6) was performed on the sections containing spheroids using microwave antigen retrieval. Detection was performed with Alexa-594 anti-rabbit antibodies (Molecular Probes), and slides were counterstained with Hoechst.

Nephron Segment Specific Staining of AK Cells in Culture:

Tubular segments were identified by use of the following markers: Proximal tubule (PT) with Fluorescein labeled Lotus tetragonolobus lectin (LTL), collecting duct (CD) with Fluorescein labeled *Dolichos biflorus* agglutinin (DBA) 1:200 for 30 minutes (Vector Laboratories); distal tubules and thick ascending limb of Henle with anti-Tamm-Horsfall Glycoprotein antibody (anti-THG) (Millipore, Chemicon), secondary antibody used for this staining NorthernLights anti-sheep IgG-NL637 (R&D systems).

Grafting of AK Cells on the Chick Embryo Chorioallantoic Membrane (CAM):

Fertile chicken eggs were obtained from a commercial supplier, and incubated at 37° C. at 60-70% humidity in a forced-draft incubator. At 3 days of incubation, an artificial air sac was established dropping the CAM. A window was opened in the shell, and the CAM exposed on 9 or 10th day of incubation. AK cells derived from AK adherent vs spheroid cultures or NCAM+/− sup-populations. AK cells were suspended in 50 μl medium and Matrigel (1:1 by volume) and pipetted into a plastic ring placed on the membrane. The egg was then sealed with adhesive tape and returned to the incubator. After one week, the graft was removed, paraffin embedded, and serially sectioned at 6 μm for histological and immunocytochemical analyses. Sample sections were stained with hematoxylin and eosin at intervals of 100-150 μm in order to find the grafted cells in the large mass of Matrigel (not shown). Biotin-labeled LTA (1:500), DBA (1:2000) (Vector Laboratories) and mouse anti-THG (1:800) (Millipore, Chemicon) were used for distinguishing parts of the renal tubules. Before immunostaining, sections were boiled for 10 minutes in 10 mM citrate buffer, PH 6.0 in a microwave oven for antigen retrieval (only for anti-THG). Endogenous peroxidates was blocked using 3% $H_2O_2$ in methanol for 10 min. The lectins and primary antibodies were subsequently stained by the avidin-biotin method, using peroxidase conjugated avidin (lectins), proceeded by anti-mouse biotin (antibody) (Vector laboratories). Controls were prepared by omitting the lectin or the primary antibody. DAB substrate kit (Zymogen) was used for detection of the peroxidase.

Double-immunocytochemistry for Ki67 (mammalian-specific monoclonal rabbit antibody, Lab Vision clone SP6) and NCAM (mouse monoclonal, Santa Cruz) was performed on the sections containing AK cells using microwave antigen retrieval. Detection was performed with Alexa-488 anti-mouse and Alexa-594 anti-rabbit antibodies (Molecular Probes), and slides were counterstained with Hoechst, and all serial sections were examined. Photomicrographs were made with digital cameras (CFW-1312M and CFW-1612C, Scion Corporation) on Olympus SZX12 and BX51 microscopes. All changes in the images (contrast, brightness, gamma, sharpening) were made evenly across the entire field, and no features were removed or added digitally.

Sphere Forming Assay:

To establish genetically marked hKEpC, HEK293 cells were initially transformed. HEK293 cells were maintained in Dulbecco's modified Eagle's medium supplemented with 10% fetal calf serum, L-glutamine, penicillin and streptomycin (Biological Industries, Israel), at 37° C. and 5% CO2. Cells were transfected using calcium phosphate with three lentiviral vectors, pHR-CMV-GFP/m-Cherry (7.5 μg), ΔR8.2 (5 μg) and pMD2.G (2.5 μg). After 6 h, the supernatants were replaced with 5 ml of fresh medium. Supernatants of transfected cells were supplemented with HEPES (pH 7.0; 50 mM final concentration), filtered through a 0.45-μm-pore-size filter, and 2 ml was placed on the targeted cells for 2 h with the addition of 8 μg/ml Polybrene (hexadimethrine bromide; Sigma) then 3 ml of fresh medium was added. These viral like particles were used to infect hKEpC cells ($2\times10^5$ cells in 60-mm-diameter dishes) Expression of reporter genes was analyzed two days post infection. GFP and m-Cherry labeled hKEpC cells were mixed in 1:1 ratio and seeded on PolyHEMA pre-coated 6 well plates, $1\text{-}2\times10^4$ cells/well.

Microarray Analysis:

Adult renal spheroids and monolayer cells were obtained from 3 different adult donors. All experiments were performed using Affymetrix HU GENE1.0st oligonucleotide arrays (url1). Total RNA from each sample was used to prepare biotinylated target DNA, according to manufacturer's recommendations. The target cDNA generated from each sample was processed as per manufacturer's recommendation using an Affymetrix GeneChip Instrument System (url2). The quality and amount of starting RNA was confirmed using an agarose gel or by Bioanalyser (Agilent). After scanning, array images were assessed by eye to confirm scanner alignment and the absence of significant bubbles or scratches on the chip surface. The signals derived from the array will be assessed using various quality assessment metrics. Details of quality control measures can be found at (url1). Gene level RMA sketch algoritm (Affymetrix Expression Console and Partek Genomics Suite 6.2) was used for crude data generation. Significantly changed genes were filtered as changed by at least 2 fold (P value 0.05). Genes were filtered and analysed using unsupervised hierarchical cluster analysis, and supervised hierarchical cluster analysis (Partek Genomics Suite and Spotfire DecisionSite for Functional Genomics; Somerville, Mass.) to get a first assessment of the data. Further processing included functional analysis and over-representation calculations based on Gene Ontology and publication data: DAVID (www.apps1.niaid.nih.gov/David/upload.asp), Ingenuity, Database for Annotation (GO), Visualization, and Integrated Discovery. Over-representation calculations are done using Ease (DAVID).

url1:www.worldwidewebdotaffymetrixdotcom/support/technical/datasheets/gene_1_0_st_datasheet.pdf
url2:www.worldwidewebdotaffymetrixdotcom/support/downloads/manuals/wt_sensetarget_label_manualdot.pdf Time Lapse Microscopy:

hKEpC were seeded on the poly-HEMA pre-coated plate. Photomicrographs were taken every 3 minutes by CLSN 410 Zeiss microscope (×10) in DIC mode. Images were stacked to the movie file by ImageJ 1.42q software.

Statistical Analysis:

Results are expressed as the mean values±STDEV. Statistical differences of two group data were compared by Student's t test. Where indicated, t test was performed after logarithmic transformation in order to achieve normality. For all statistical analysis, the level of significance was set as P<0.05.

Example 1

Adherent hFK Cell Cultures

Following the retrieval of a small specimen of hAK from nephrectomized patients, tissue was dissociated into a single cell suspension and cultured in low densities in T75 flasks so as to allow clonal growth (see scheme in FIG. 1). To achieve expansion to a confluent adherent monlayer culture (P0), low cell numbers were initially grown using either serum containing media (SCM) or defined serum free media (SFM). Cell growth was initiated from small cell foci. However, while both media enabled cell expansion, SFM promoted more concentric, well defined expansion and SCM displayed rapid expansion in a less-organized manner (FIGS. 2A-F). Staining of cultures for segment-specific markers [lotus tetragonolobus (LTA)-proximal tubules; Tamm-Horsfall glycoprotein (THG)-distal tubules; DBA-collecting tubules] revealed the presence of heterogeneous tubule cell types with predominance of proximal (70%) and distal (20%) tubules and to a lesser extent collecting ducts (<10%; FIGS. 3A-D). Staining of renal proximal tubular epithelial cells (RPTEC) and human foreskin fibroblasts (HFF) were used as positive and negative controls respectively (FIGS. 3E-J). This heterogeneity was preserved along hKEpC culture passages (P3-P5)—FIGS. 4A-F.

Analysis of renal epithelial segment specific gene (aminopeptidase A(ENPEP), aquaporin-1 (AQP1), aquaporin-3 (AQP3), Na/Cl co-transporter (NCCT) and podocin) expression in the primary kidney cultures compared to human foreskin fibroblasts (HFF) indicated the tubular epithelial nature of the cells as illustrated in Table 1. Shown are relative quantification (RQ) values, normalized to expression values of HFF (which therefore equal 1). Two different P) hKEpC cultures are shown to express all the nephron segment-specific genes: proximal tubule—aminopeptidase-A (ENPEP) and Aquaporin-(AQP1)-collecting duct—Aquaporin-3 (AQP3), distal convoluted tubule—NA/Cl co-transporter (NCCT), podocyte—Podocin.

TABLE 1

Gene expression in RQ values

|  | HFF | hKEpC#1 | hKEpC#2 |
| --- | --- | --- | --- |
| ENPEP | 1 | 28.36 | 9.40 |
| AQP1 | 1 | 281.14 | 70.19 |
| AQP3 | 1 | 6.34 | 1.97 |
| NCCT | 1 | 3845.58 | 3387.39 |
| Podocin | Undetectable | Detectable | Detectable |

Analysis of renal progenitor gene expression in the heterogeneous P0 adherent SCM and SFM cultures showed similar gene levels (FIGS. 5A-E). Cells were then harvested and propagated and expanded as adherent cultures in SFM/SCM or subjected to sphere formation and limiting dilutions to assess for clonogenicity in various culture conditions (see FIG. 1).

Example 2

Low-Attachment Conditions in Heterogeneous hAK Cultures Promote Formation of 'Nephrospheroids'

The present inventors considered that culture conditions that support proliferation of human kidney cells that form spheroids may represent a strategy for isolation of cells with progenitor potential. Accordingly, heterogeneous P0 adherent SCM and SFM cultures originating from five hAK samples were subjected to low attachment conditions—specifically they were seeded on polyHEMA plates at a density of 20-40,000 viable cells/ml.

After 7-10 days, floating cellular aggregates, termed nephrospheroids or hKEpC spheroids, 100-130 micrometer in diameter, were obtained from 10 of the 10 cases (FIG. 6A). Primary kidney-spheres, once enzymatically disaggregated into single cells and replated at a density of 20,000 cells/ml in ultra-low attachment plates could give rise to secondary spheres within 5-7 days of culture. Having determined that P2 spheroids could be reproducibly generated following the seeding of $2 \times 10^4$ cells/2 ml of P1 monolayer hKEpCs, the present inventors determined hKEpC spheroid formation after long-term monolayer culture and observed reproducible generation of P6 spheroids following seeding of similar cell numbers of P5 monolayer hKEpCs (FIG. 6B). Interestingly, a comparison between low and high passage hKEpCs spheroids showed the latter to display a well-organized, more condensed and "true" sphere-like morphology. In addition, it was found that a significantly higher number of spheroids were generated at P6 compared to P2 cultures (FIG. 6C). Close examination of this difference revealed it to be attributed mainly to formation of small size spheroids (<15 μm), rather then medium size (15-130 μm) or larger ones (>130 μm) (FIG. 6D).

Origin of hKEpC Spheroids:

In order to analyze whether hKEpC spheroids are of clonal origin, kidney-derived cells from two donors were grown as a monolayer and stably labeled with either red or green fluorescent proteins using lentivirus-based vectors, directing constitutive expression of mCherry and GFP, respectively. For efficient infection and antibiotic selection of monolayer hKEpC, cells were propagated to P2-P3. Fluorescent hKEpC were detached, mixed at a ratio of 1:1 and subjected to low-attachment conditions at low densities $10^4$ cells/well to generate spheroids. Continuous microscopic examination from 7-10 days to six weeks after seeding revealed that spheroids contained both red and green cells. More than 75% of cells in each kidney-spheroid were comprised of one color (FIG. 7), suggesting that aggregation into hKEpC spheroids had occurred and that cells were not entirely clonally derived. In addition to genetic labeling, time-lapse microscopy was utilized to follow initial events after hKEpC seeding ($2 \times 10^4$ cells/well) in non-adherent conditions, as cells were filmed every 3 minutes for 48 hours. Cell collision and aggregation were noticed to occur within five hours after seeding, indicating this as the initiating process for spheroid formation.

Phenotypic Characterization of hKEpC Spheroids:

The present inventors initially determined whether the generation of hKEpC spheroids promoted the expression of 'stemness' genes.

Elevated expression of Pax2, Sall1, Six2, Wt1 as well as the pluripotency gene, Nanog, when compared to adherent culture (FIG. 8D) was found. Moreover, this expression profile was especially prominent when spheroids were generated from hAK cells grown in SFM and not SCM (including Six2), while expansion in SFM adherent cultures did not significantly promote renal progenitor markers by comparison to SCM adherent cultures (FIGS. 8E-H).

Interestingly, among genes characteristic of the early ureteric lineage a strong elevation in kidney-spheroids of the heparan sulfate proteoglycan GPC3, an extra-cellular matrix (ECM) molecule, which functions in the ureteric bud niche was found (FIG. 8I), but expression of the other ureteric lineage genes (Wnt11 and c-Ret) was undetectable (data not shown). Finally, generation of kidney-spheroids after long-term monolayer expansion (P6) also resulted in significant re-expression of the renal progenitor genes (FIG. 8J). Thus, in contrast to monolayer cells hKEpC spheroids promoted, at least in part, expression of renal developmental markers and 'stemness' profile.

Flow cytometry was used (FIG. 9A) to analyze the percentage of cells expressing the epithelial, renal and mesenchymal stem cell antigens EpCAM, CD24, CD133, CD44 (15) in spheroid and monolayer hKEpC. High expression levels of CD24 and CD44 (80-100% of cells) in both spheroids and monolayer cells was found (FIG. 9A and FIG. 9B), while EpCAM and CD133 levels found to be further elevated in spheroids indicating mostly an EpCAM$^+$CD24$^+$CD133$^+$CD44$^+$ phenotype of spheroid cells. In addition, analysis of the activity of aldehyde dehydrogenase1 (ALDH1), an enzyme which increased activity has been detected in stem/progenitor cell populations, showed significantly higher levels in hKEpC spheroid cells compared to monolayer counterparts (FIG. 9C). It was found that 29.93±11.78% of spheroid cells displayed high levels of ALDH1 activity, compared to 8.06±4.53% of monolayer cells.

Thus, hKEpC spheroids have a distinct antigenic profile with enhanced ALDH1 activity. Global transcriptional changes associated with kidney spheroid formation: Having illuminated specific characteristics of hKEpC spheroids the present inventors wanted to assess on a global level the transcriptional alternations taking place in relation with spheroid formation. For this spheroid and monolayer hKEpC were generated from three different human adult kidney sources and their global gene expression profile using oligonucleotide microarrays were compared. Unsupervised clustering (Partek 6.5) of the entire human microarray data set clearly distinguished among samples separating them into two major groups: hKEpC spheroids and hKEpC grown as monolayer and indicating a different biological entity and fundamental difference in gene expression patterns (FIG. 10A). Kidney spheroids were closer to each other rather than to their monolayer counterpart of the same adult kidney origin. 825 genes differentially expressed by spheroid and monolayer hKEpC (>2 fold change, ANOVA, $P<0.05$) were identified. These included 477 genes upregulated and 348 downregulated in spheroids compared to monolayer cells (FIG. 10B). The 20 genes most highly expressed in hKEpC spheroids and monolayer cells are respectively shown in Table 2.

TABLE 2

| Gene category | Gene name | Symbol | Fold-Change | RefSeq | Probeset ID |
|---|---|---|---|---|---|
| | Up-regulated | | | | |
| | chromosome 9 open reading frame 71 | C9orf71 | 43.20 | NM_153237 | 8161610 |
| | low density lipoprotein receptor-related protein 2 | LRP2 | 18.30 | NM_004525 | 8056611 |
| ECM protein | spondin 2 | SPON2 | 15.33 | NM_012445 | 8098870 |
| sodium ion transport | solute carrier family 10 | SLC10A2 | 12.97 | NM_000452 | 7972692 |
| | polymeric immunoglobulin receptor | PIGR | 11.75 | NM_002644 | 7923929 |
| | adenylate cyclase 5 | ADCY5 | 11.55 | NM_183357 | 8090070 |
| | transmembrane protein 176A | TMEM176A | 11.50 | NM_018487 | 8137264 |
| | aldehyde dehydrogenase 1 family, member A1 | ALDH1A1 | 11.30 | NM_000689 | 8161755 |
| | transmembrane protease, serine 4 | TMPRSS4 | 9.44 | NM_019894 | 7944164 |
| | leucine-rich repeat kinase 2 | LRRK2 | 8.57 | NM_198578 | 7954810 |
| | aquaporin 1 | AQP1 | 8.21 | NM_198098 | 8132118 |
| | solute carrier family 17, member 1 | SLC17A1 | 7.91 | NM_005074 | 8124337 |
| | V-set domain containing T cell activation inhibitor 1 | VTCN1 | 7.24 | NM_024626 | 7918936 |
| | solute carrier family 27 | SLC27A2 | 6.92 | NM_003645 | 7983650 |
| | solute carrier family 34, member 2 | SLC34A2 | 6.90 | NM_006424 | 8094441 |
| ECM | mucin 20 | MUC20 | 6.60 | NM_152673 | 8084895 |
| | acyl-CoA synthetase medium-chain family member 3 | ACSM3 | 6.41 | NM_005622 | 7993756 |
| | aldo-keto reductase family 1, member B10 | AKR1B10 | 6.19 | NM_020299 | 8136336 |
| | phospholipase A1 member A | PLA1A | 6.13 | NM_015900 | 8081890 |
| | complement component 4A | C4A | 6.09 | NM_007293 | 8118409 |
| | Down-regulated | | | | |
| | solute carrier family 14 | SLC14A1 | −16.06 | NM_001128588 | 8021081 |
| | serpin peptidase inhibitor | SERPINE1 | −11.15 | NM_000602 | 8135069 |
| | Thy-1 cell surface antigen | THY1 | −6.99 | NM_006288 | 7952268 |
| | filaggrin | FLG | −6.82 | NM_002016 | 7920165 |

TABLE 2-continued

| Gene category | Gene name | Symbol | Fold-Change | RefSeq | Probeset ID |
|---|---|---|---|---|---|
| | lysyl oxidase | LOX | −6.17 | NM_002317 | 8113709 |
| | cadherin 13, H-cadherin | CDH13 | −5.41 | NM_001257 | 7997504 |
| | metallothionein 1L | MT1L | −5.25 | NR_001447 | 7995793 |
| | metallothionein 1A | MT1A | −5.20 | NM_005946 | 7995806 |
| | plasminogen activator, tissue | PLAT | −4.90 | NM_000930 | 8150509 |
| | semaphorin 7A | SEMA7A | −4.89 | NM_003612 | 7990345 |
| | serpin peptidase inhibitor, clade B | SERPINB7 | −4.88 | NM_003784 | 8021623 |
| | DNA-damage-inducible transcript 4 | DDIT4 | −4.85 | NM_019058 | 7928308 |
| | small nucleolar RNA, C/D box 30 | SNORD30 | −4.67 | NR_002561 | 7948900 |
| | cyclin A2 | CCNA2 | −4.66 | NM_001237 | 8102643 |
| | histone cluster 1, H2bm | HIST1H2BM | −4.63 | NM_003521 | 8117594 |
| | small nucleolar RNA, C/D box 25 | SNORD25 | −4.57 | NR_002565 | 7948910 |
| | sema domain, immunoglobulin domain (Ig) | SEMA3A | −4.53 | NM_006080 | 8140668 |
| | small nucleolar RNA, C/D box 74 | SNORD74 | −4.50 | NR_002579 | 7922418 |
| | kynureninase (L-kynurenine hydrolase) | KYNU | −4.47 | NM_003937 | 8045539 |
| | cyclin B2 | CCNB2 | −4.45 | NM_004701 | 7983969 |

To infer the function of the 825 differentially expressed genes, the Gene Ontology (GO) enrichment analysis tool and DAVID were used. Up and down regulated genes in hKEpC spheroids were categorized into cellular processes, according to Partek (FIG. 10C) and DAVID (Table 3), showing the most significantly elevated genes to group into cell-cell adhesion/ECM/cell recognition, ion transport, regulation of cellular component biogenesis, while down-regulated genes were related to cell growth/mitosis/cell cycle and cell locomotion.

TABLE 3

| | Count |
|---|---|
| Up-regulated | |
| cell adhesion | 23 |
| sodium ion transport | 8 |
| cell-cell adhesion | 10 |
| anion transport | 7 |
| cell motion | 13 |
| response to hormone stimulus | 11 |
| phosphate transport | 3 |
| regulation of cell motion | 7 |
| cell migration | 8 |
| extracellular structure organization | 6 |
| cellular aldehyde metabolic process | 3 |
| cell motility | 8 |
| cell morphogenesis involved in differentiation | 7 |
| regulation of cellular localization | 7 |
| Down-regulated | |
| M phase | 47 |
| cell cycle | 67 |
| cell cycle phase | 51 |
| cell cycle process | 57 |
| mitosis | 37 |
| mitotic cell cycle | 44 |
| cell division | 38 |
| chromosome organization | 26 |
| cell proliferation | 23 |
| meiosis | 9 |
| blood vessel morphogenesis | 13 |
| blood vessel development | 14 |
| vasculature development | 14 |
| chromatin organization | 14 |
| regulation of locomotion | 9 |
| regulation of cell motion | 9 |
| cell migration | 11 |
| regulation of cell migration | 8 |
| cell motion | 15 |
| growth | 8 |
| localization of cell | 11 |
| cell motility | 11 |

Table 4 further elaborates 23 genes categorized in biological adhesion, which were up-regulated in spheroid cells (DAVID, p<0.00001).

TABLE 4

| Cell and biological adhesion | | | |
|---|---|---|---|
| Symbol | Gene name | Gene assignment | Fold change |
| CLDN7 | claudin 7 | Involved in the formation of tight junctions between epithelial cells | 2.74 |

TABLE 4-continued

Cell and biological adhesion

| Symbol | Gene name | Gene assignment | Fold change |
|---|---|---|---|
| PCDHB5 | Protocadherin beta-5 | Member of the protocadherin beta gene cluster | 3.32 |
| CLDN3 | Claudin 3 | Member of the claudin family, is an integral membrane protein and a component of tight junction strands. | 3.93 |
| CNTN6 | contactin 6 | Contactins mediate cell surface interactions during nervous system development. Participates in oligodendrocytes generation by acting as a ligand of NOTCH1. | 3.09 |
| PKHD1 | polycystic kidney and hepatic disease 1 | Localized predominantly at the apical domain of polarized epithelial cells, suggesting it may be involved in the tubulogenesis and/or maintenance of duct-lumen architecture. | 3.38 |
| PCDHB2 | protocadherin beta 2 | The extracellular domains interact in a homophilic manner to specify differential cell-cell connections. | 2.94 |
| CDH1 | E-cadherin (epithelial) | cell adhesion molecule | 3.27 |
| CX3CL1 | hemokine (C-X3-C motif) ligand 1 | CX3CL1 elicits its adhesive and migratory functions by interacting with the chemokine receptor CX3CR1 | 2.86 |
| CXADR | coxsackie virus and adenovirus receptor | | 2.95 |
| BCL2L11 | BCL2-like 11 (apoptosis facilitator) | | 2.42 |
| SEMA5A | sema domain seven thrombospondin repeats | | 4.01 |
| PVRL4 | poliovirus receptor-related 4 | Involved in cell adhesion through trans-homophilic and -heterophilic interactions. It is a single-pass type I membrane protein. | 3.18 |
| ARVCF | Armadillo repeat protein deleted in velo-cardio-facial syndrome | Member of the catenin family which play an important role in the formation of adherens junction complexes, which are thought to facilitate communication between the inside and outside environments of a cell. | 2.22 |
| CDH16 | cadherin 16, KSP-cadherin | cell adhesion molecule | 2.99 |
| AGT | angiotensinogen (serpin peptidase inhibitor, clade A, member 8) | Essential component of the renin-angiotensin system (RAS) | 5.67 |
| ITGB6 | integrin beta 6 | Integrin alpha-V/beta-6 is a receptor for fibronectin and cytotactin. | 3.41 |
| VNN1 | vanin 1 | May play a role in oxidative-stress response | 4.79 |
| RHOB | ras homolog gene family member B | Mediates apoptosis in neoplastically transformed cells after DNA damage. Affects cell adhesion and growth factor signaling in transformed cells. | 2.58 |
| CNTN4 | contactin 4 | Member of the immunoglobulin superfamily. It is a glycosylphosphatidylinositol (GPI)-anchored neuronal membrane protein that functions as a cell adhesion molecule. | 2.61 |
| GPNMB | glycoprotein (transmembrane) nmb | transmembrane glycoprotein | 6.03 |
| SPON2 | Spondin 2 | Extracellular matrix protein | 15.33 |
| CHL1 | cell adhesion molecule with homology to L1CAM | cell adhesion molecule | 4.58 |
| CEACAM1 | carcinoembryonic antigen-related cell adhesion molecule | cell adhesion molecule | 2.07 |

Thus, hKEpC spheroids generated a quiescent niche enriched in cell-cell and cell matrix interactions. The quiescent nature of spheroids was confirmed by analysis of proliferating cells in whole spheroids fixed and embedded in paraffin and stained for hematoxylin and eosin (FIG. 11A) and for the cell proliferation marker, Ki-67 (FIG. 11B). All hKEpC spheroids exhibited a low proliferation index of <10% of Ki-67-positive cells per spheroid/section, indicative of the quiescent nature of the spheroids.

Example 4

Heterogeneous hAK Cells Cultured in Fetal Kidney Conditioned Media Show Enhanced Clonogenicity Following the observation that heterogeneous cultures of kidney epithelial cells maintain the ability to form spheres, the present inventors analyzed culture conditions that enhance cells' clonogenic capacities and would allow for clonal analysis of hAK cell subpopulations. Cells were plated in limiting dilution (LD) concentrations under 4 different growth conditions: a) SCM, b) SFM, c) culture expanded in SCM and LD analysis performed in SFM, d) SCM in 1:1 ratio with fetal kidney conditioned media (FKCM). Analysis of the number of colonized wells, recorded after 4 weeks, showed that SCM promotes higher clonogenic capacities compared to SFM. This was especially evident when combined with FKCM (condition d) (FIGS. 12A-C). FKCM clones showed improved viability and confluence as opposed to SCM (FIGS. 13A-D). Clonogenic expansion indicative of self-renewal could be performed for more than 11 passages.

Example 5

NCAM1 Expressing Cells Isolated from Heterogeneous hAK Cultures are Highly Clonogenic and Preferentially Form Spheres Following elucidation of various culture conditions that allow for enhanced expression of the renal progenitor genes, clonogenic capabilities and nephrospheroid formation the present inventors determined surface markers that could identify cells within the heterogeneous hAK cultures preferentially exhibiting these characteristics. Accordingly, cell subpopulations positive for surface markers which have been shown to mark the renal progenitor population of the developing human kidney such as NCAM1 and FZD7 (10, 11) were sorted. NCAM1 which during nephrogenesis is localized to cells of the MM and its early derivatives, including condensed mesenchyme and early nephron, is not expressed in the adult kidney in vivo (11, 17, 18). Efficient fractionation of NCAM+ cells was achieved with FACS sorting (FIGS. 14A-C) and to a lesser extent via microbeads. Analysis of renal 'stemness' genes in NCAM+ cells compared to NCAM− fraction obtained from heterogeneous cultures of five different hAK revealed overexpression of the early renal epithelial progenitor markers (Six2, Osr1, Sall1, Pax2 and Wt1) and early surface antigens (FZD7, AVR2b) (11), polycomb group (Bmi-1, Ezh2), Wnt pathway (Beta-catenin, FZD7) as well the pluripotency marker, Oct4 (FIGS. 15A-E). Analysis for renal differentiation markers revealed elevated aminopeptidase (ENPAP) and aquaporin1 (AQP1) and low Na/Cl co-transporter (NCCT) and aquaporin3 (AQP3) as well as high vimentin and low E-cadherin, all indicating NCAM+ cells to originate from the proximal tubule (FIGS. 15A-E)

Having identified the unique clonogenic ability of hAK cells cultured with FKCM, the present inventors next examined both the ability of NCAM+ and NCAM-cells to form single cell clones under these conditions as well as their proliferative capacity in culture. Experiments performed on cultures originating from 3 different kidneys revealed the NCAM+ fraction to be highly clonogenic in all instances (FIGS. 16A-C). Although highly clonogenic, NCAM+ cells were found to be less proliferative on MTS proliferation assay compared to the negative counterpart (FIG. 16D). Sphere-forming activity in the NCAM+ cell population sorted from heterogeneous hAK cultures was then assessed. Strikingly, immediately after sorting of low-passage cultures, only NCAM+ cells generated spheres while the NCAM− fraction was devoid of this capacity. Short-term expansion of NCAM+ cells after sorting resulted in the appearance of spheres in the NCAM− population; nevertheless, well-defined spheres were exclusively observed in the NCAM+ cells (FIGS. 16E-J). Analysis of sorted populations from high-passage cultures showed both the NCAM+ and NCAM− fractions to possess sphere-forming abilities (data not shown)). Accordingly, while well-defined spheres generated from NCAM+ cells in low-passage cultures demonstrated enhanced expression of the renal progenitor genes compared to spheres formed by NCAM− cells and also to an adherent NCAM+ fraction, in high-passage cultures both NCAM+ and NCAM− spheres showed similar elevated gene levels when compared to adherent NCAM+ cells (data not shown). Thus, NCAM strongly enriched for sphere-forming capability in low-passage heterogeneous cultures. In high-passage cultures, sphere-formation irrespective of NCAM expression enriches for the renal progenitor genes.

Example 6

Figure 17I:
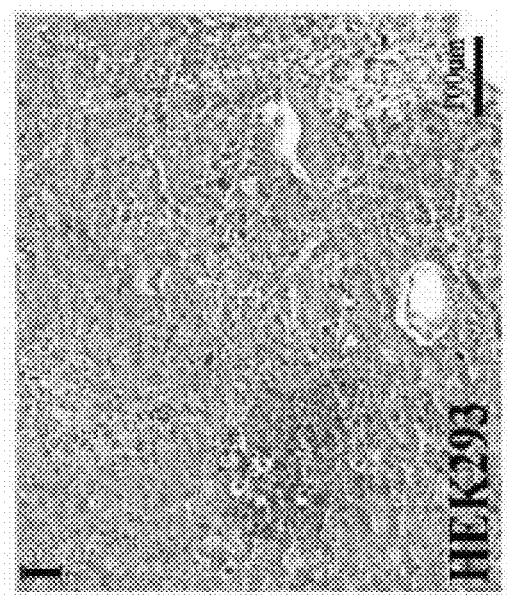
Figure 17H:
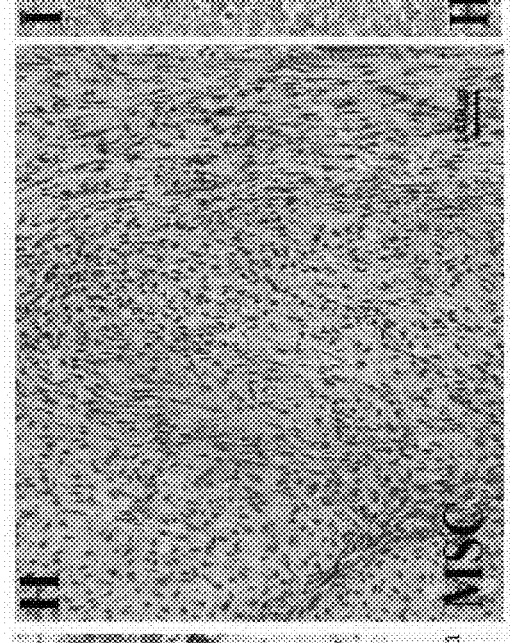
Figure 17G:
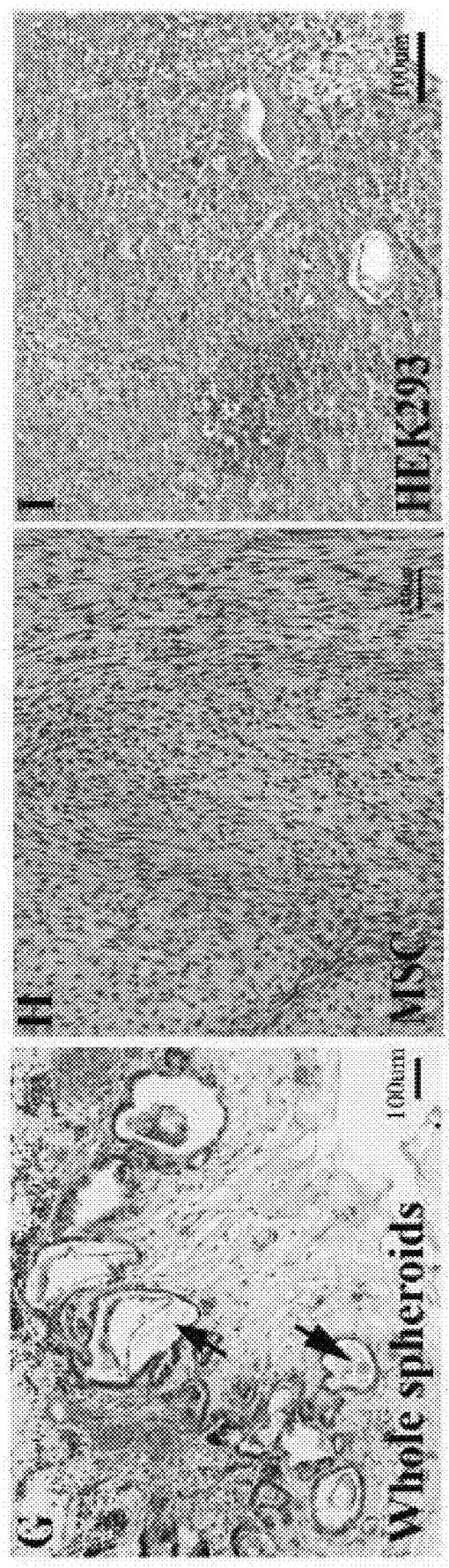
Figure 17K:
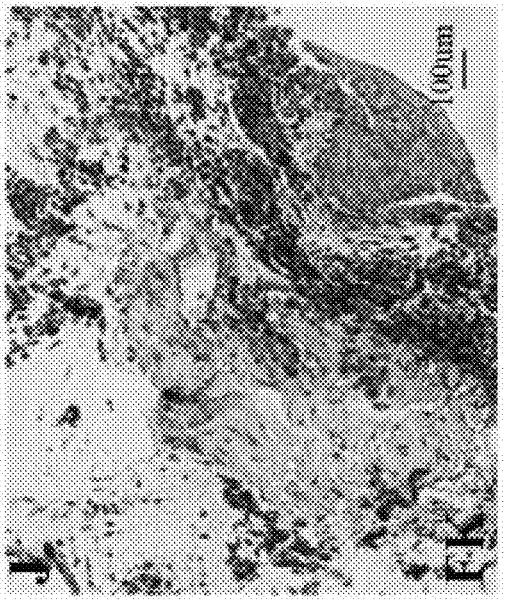
Figure 17J:
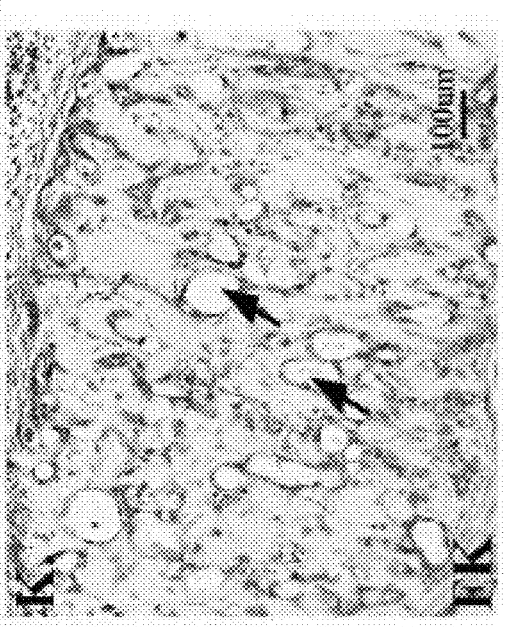

In Vivo Generation of Human Tubular Structures in the Chick Embryo by Nephrospheroids and NCAM+ Cells Having determined that hKEpC spheroids have enhanced renal "stemness" profile and recapitulate a microenvironment rich in ECM and cell contact molecules the present inventors tested whether this leads to improved functional potency to generate renal structures. Accordingly, human cell grafting was performed onto the chorioallantoic membrane (CAM) of the chick embryo and their fate 7 days post-implantation was analyzed (FIG. 17A-k). Chick embryos were grafted with either whole hKEpC spheroids, or single cell suspensions of dissociated spheroid-cells (immediately after disassociation) and monolayer hKEpC. The suspended cells are especially important as they represent an injectable form of cells. Implantation of whole human kidney-spheroids onto the CAM resulted in tubule formation (FIG. 17G). Comparison of single cell implantation of spheroid and monolayer hKEpC demonstrated that grafts generated from spheroid cells were much bigger then their counterparts (FIGS. 17A-B). H&E staining revealed robust tubule formation capacity by spheroid-cells, e.g. $0.43 \times 10^6$ spheroid cells induced formation of multiple tubular structures, while few tubuli were observed in grafts generated by similar numbers of monolayer hKEpC (FIGS. 17C-D). Additional experiments were performed to determine whether hKEpC spheroids generated after long-term expansion of monolayer cells (P6) can recapitulate tubule formation. $0.43 \times 10^6$ dissociated single spheroid cells grafted onto the CAM reconstituted tubular structures, while long-term expanded monolayer hKEpC (P6) completely failed to generate similar structures (FIGS. 17E-F). Importantly, grafting of control cell types, mesenchymal stem cells (MSCs) and human embryonic kidney cell line (HEK293) generated disorganized cell masses (FIGS. 17H-I), indicating that only kidney-derived cells bear nephrogenic potential in this model. Interestingly, when using human fetal kidney (FK) cells as additional controls no tubular formation was observed after grafting of $1.25 \times 10^6$ FK cells (FIG. 17J), while grafting of $2.5 \times 10^6$ FK cells (FIG. 17K) showed tubular formation. Therefore much fewer ($0.43 \times 10^6$) adult kidney spheroid cells generate tubular structures further emphasizing there high tubulogenic capacity.

To better define the tubular structures that were formed by dissociated spheroid hKEpC, graft sections were stained for segment-specific tubular markers (LTA, proximal; THG, distal; DBA, distal/collecting). It was found that reconstituted renal structures showed LTA, THG and DBA positive tubules and were reminiscent of a wide adult human tubular spectrum (FIGS. 18A-D). To clarify specificity of DBA expression immunofluorescent staining was performed and DBA(+) tubules were found to comprise a portion of the reconstituted tubules (FIG. 18D). Spheroid-cells obtained from high-passage cultures also showed more than one type of differentiated tubules with positive staining of the THG and DBA markers and to a much lesser extent LTA staining (FIGS. 19A-C). Thus, hKEpC spheroids enhance functional potency for tubule formation.

The regenerative ability of NCAM+ sorted, adherent cells was also analyzed. In this experiment, strong tubular reconstitution by $0.43 \times 10^6$ NCAM$^+$ cells was observed with the NCAM− fraction failing to form similar structures (FIGS. 20A-F). Thus, low numbers of both spheroid- and sorted NCAM+ cells can recapitulate kidney structures in vivo indicative of high renal potential.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. Weissman I. The ISSCR: who are we and where are we going? Cell Stem Cell. 2009; 5:151-153.
2. Kondo M, Wagers A J, Manz M G, et al. Biology of hematopoietic stem cells and progenitors: implications for clinical application. Annu Rev Immunol. 2003; 21:759-806.
3. Blanpain C, Fuchs E. Epidermal homeostasis: a balancing act of stem cells in the skin. Nat Rev Mol Cell Biol. 2009; 10:207-217.
4. Barker N, van de Wetering M, Clevers H. The intestinal stem cell. Genes Dev. 2008; 22:1856-1864.
5. Nishinakamura R. Stem cells in the embryonic kidney. Kidney Int. 2008; 73:913-917.
6. Hartman H A, Lai H L, Patterson L T. Cessation of renal morphogenesis in mice. Dev Biol. 2007; 310:379-387.
7. Metsuyanim S, Pode-Shakked N, Schmidt-Ott K M, et al. Accumulation of malignant renal stem cells is associated with epigenetic changes in normal renal progenitor genes. Stem Cells. 2008; 26:1808-1817.
8. Humphreys B D, Valerius M T, Kobayashi A, et al. Intrinsic epithelial cells repair the kidney after injury. Cell Stem Cell. 2008; 2:284-291.
9. Dressler G R. Advances in early kidney specification, development and patterning. Development. 2009; 136: 3863-3874.
10. Dekel B, Metsuyanim S, Schmidt-Ott K M, et al. Multiple imprinted and stemness genes provide a link between normal and tumor progenitor cells of the developing human kidney. Cancer Res. 2006; 66:6040-6049.
11. Metsuyanim S, Harari-Steinberg O, Buzhor E, et al. Expression of stem cell markers in the human fetal kidney. PLoS One. 2009; 4:e6709.
12. Wang T Y, Sen A, Behie L A, Kallos M S. Dynamic behavior of cells within neurospheres in expanding populations of neural precursors. Brain Res 2006; 1107:82-96.
13. Goldstein A S, Lawson D A, Cheng D, Sun W, Garraway I P, Witte O N. Trop2 identifies a subpopulation of murine and human prostate basal cells with stem cell characteristics. Proc Natl Acad Sci USA 2008; 105:20882-20887.
14. Lawson D A, Xin L, Lukacs R U, Cheng D, Witte O N. Isolation and functional characterization of murine prostate stem cells. Proc Natl Acad Sci USA 2007; 104:181-186.
15. Dontu G, Abdallah W M, Foley J M, Jackson K W, Clarke M F, Kawamura M J, Wicha M S. In vitro propagation and transcriptional profiling of human mammary stem/progenitor cells. Genes Dev 2003; 17:1253-1270.
16. Bez A, Corsini E, Curti D, Biggiogera M, Colombo A, Nicosia R F, Pagano S F, Parati E A. Neurosphere and neurosphere-forming cells: Morphological and ultrastructural characterization. Brain Res 2003; 993:18-29.
17. Klein G, Langegger M, Goridis C, and Ekblom P, Neural cell adhesion molecules during embryonic induction and development of the kidney. Development, 1988. 102(4): p. 749-61.
18. Bard J B, Gordon A, Sharp L, and Sellers W I, Early nephron formation in the developing mouse kidney. J Anat, 2001. 199(Pt 4): p. 385-92.
19. Abbate M, Brown D, Bonventre J V. Expression of NCAM recapitulates tubulogenic development in kidneys recovering from acute ischemia. Am J Physiol. 1999; 277:F454-463
20. Sagrinati C, Netti G S, Mazzinghi B, et al. Isolation and characterization of multipotent progenitor cells from the Bowman's capsule of adult human kidneys. J Am Soc Nephrol. 2006; 17:2443-2456.

We claim:

1. A method for forming tubular structures in the kidney of a subject in need thereof, comprising:
   expanding human kidney epithelial cells from a human adult kidney in a first culture medium under adherent conditions, wherein the first culture medium is a serum containing medium comprising at least one growth factor comprising IMDM supplemented with 10% FBS, 1% L-glutamine, 1% Pen-Strep, and growth factors: 50 ng/ml of bFGF, 50 ng/ml of EGF, and 5 ng/ml of SCF;
   culturing the cells in a second culture medium under non-adherent conditions, thereby generating a plurality of nephrospheroid cells, wherein the second culture medium is a serum free medium comprising 500 ml DMEM:F12 in a 1:1 ratio, 1% pen-strep, 2 ml B27 supplement, 4 µg/ml heparin, 1% non-essential amino acids, 1% sodium pyruvate, 1% L-glutamine, 1 ml lipid mix, 5 ml of 100× N2 supplement, 10 ng/ml FGF, 20 ng/ml EGF, and 5 ml growth factor mix; wherein a 200 ml solution of growth factor mix comprises 100 ml DMEM:F12, 4 ml of 30% glucose, 200 mg transferin, 50 mg insulin in 20 ml of water, 19.33 mg putrescine in 20 ml ddw, 200 µl of 0.3 mM sodium selenite, and 20 µl of 2 mM progesterone;
   isolating a population of nephrospheroid cells from the second culture medium; and
   administering to the subject a therapeutically effective amount of the isolated nephrospheroid cells by injection to a damaged kidney of the subject.

2. The method according to claim 1 further comprising removing kidney cells from a subject suffering from renal damage, prior to expanding the cells.

3. The method according to claim 1 further comprising testing a nephrospheroid cell for the presence of a renal progenitor cell marker.

4. The method according to claim 3 wherein the nephrospheroid cells express NCAM.

5. The method according to claim 4 wherein the nephrospheroid cells have increased levels of sall1, pax2, six2 and WT1.

6. The method according to claim 1 wherein the isolated nephrospheroid cells are administered with a pharmaceutically acceptable carrier.

7. The method according to claim 1 wherein the subject suffers from renal failure.

8. The method according to claim 1 wherein the subject suffers from acute or chronic kidney disease, diabetic nephropathy, renal disease associated with hypertension, hypertensive acute tubular injury, interstitial nephritis, Aplasia, dysplasia, obstructive uropathy, reflux nephropathy, Juvenile nephronophtisis, autosomal recessive polycystic kidney disease, Alport, Cystinosis, Primary Hyperoxaluria, Glomerulonephritides, Focal Segmental Glomerulosclerosis, systemic lupus erythematosus, Henoch-Schönlein purpura, or Hemolytic-uremic syndrome.

9. The method according to claim 1 wherein at least 50% of the nephrospheroid cells are NCAM+.

10. The method according to claim 9 wherein the nephrospheroid cells are EpCAM+.

11. The method according to claim 1 wherein the cells from the human adult kidney are expanded for two passages or fewer.

12. The method according to claim 1 wherein the tubular structures are proximal and distal tubules.

* * * * *